United States Patent
Hanes et al.

(10) Patent No.: US 9,889,208 B2
(45) Date of Patent: Feb. 13, 2018

(54) LIPID-BASED DRUG CARRIERS FOR RAPID PENETRATION THROUGH MUCUS LININGS

(71) Applicant: The Johns Hopkins University, Baltimore, MD (US)

(72) Inventors: Justin Hanes, Baltimore, MD (US); Kannie Wai Yan Chan, Baltimore, MD (US); Michael T. McMahon, Columbia, MD (US); Ming Yang, Townson, MD (US); Tao Yu, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 321 days.

(21) Appl. No.: 14/397,828

(22) PCT Filed: May 6, 2013

(86) PCT No.: PCT/US2013/039731
§ 371 (c)(1),
(2) Date: Oct. 29, 2014

(87) PCT Pub. No.: WO2013/166498
PCT Pub. Date: Nov. 7, 2013

(65) Prior Publication Data
US 2015/0086484 A1   Mar. 26, 2015

Related U.S. Application Data

(60) Provisional application No. 61/642,776, filed on May 4, 2012.

(51) Int. Cl.
A61K 9/127   (2006.01)
A61K 47/48   (2006.01)
(Continued)

(52) U.S. Cl.
CPC ...... *A61K 47/48815* (2013.01); *A61K 9/1271* (2013.01); *A61K 31/704* (2013.01); *A61K 47/6911* (2017.08); *A61K 49/1812* (2013.01)

(58) Field of Classification Search
CPC ............................................ A61K 9/127
See application file for complete search history.

(56) References Cited

U.S. PATENT DOCUMENTS

| 4,997,652 A | 3/1991 | Wong |
| 5,013,556 A | 5/1991 | Woodle |

(Continued)

FOREIGN PATENT DOCUMENTS

| WO | 9207866 | 5/1992 |
| WO | 9742962 | 11/1997 |

(Continued)

OTHER PUBLICATIONS

Deosarkar, et al.., "Polymeric particles conjugated with a ligand to VCAM-1 exhibit selective, avid, and focal adhesion to sites of atherosclerosis", Biotech. Bioeng., 101(2):400-7 (2008).

(Continued)

*Primary Examiner* — Gollamudi Kishore
(74) *Attorney, Agent, or Firm* — Pabst Patent Group LLP

(57) ABSTRACT

Mucus-penetrating liposomal nanoparticles and methods of making and using thereof are described herein. The nanoparticles contain one or more lipids, one or more PEG-conjugated lipids, and optionally one or more additional materials that physically and/or chemically stabilize the particles. The nanoparticle have an average diameter of about 100 nm to about 300 nm, preferably from about 100 nm to about 250 nm, more preferably from about 100 nm to about 200 nm. The particles are mobile in mucus. The liposomes can further contain one or more therapeutic, prophylactic, and/or diagnostic agent to be delivered to a (Continued)

mucosal surface, such as the CV tract, the colon, the nose, the lungs, and/or the eyes. The liposomes can further contain one or more CEST agents to allow real time imaging of the particles in a live animal. The particles may also further contain an imaging agent, such as a fluorescent label.

20 Claims, 4 Drawing Sheets

(51) Int. Cl.
A61K 31/704 (2006.01)
A61K 49/18 (2006.01)
A61K 47/69 (2017.01)

(56) References Cited

U.S. PATENT DOCUMENTS

| | | | |
|---|---|---|---|
| 5,356,633 A * | 10/1994 | Woodle | A61K 9/1271 424/423 |
| 5,540,930 A | 7/1996 | Guy | |
| 5,567,435 A | 10/1996 | Hubbell | |
| 5,576,311 A | 11/1996 | Guy | |
| 5,578,325 A | 11/1996 | Domb | |
| 5,696,298 A | 12/1997 | Emanuele | |
| 5,710,135 A | 1/1998 | Leenders | |
| 5,869,130 A | 2/1999 | Ferrier | |
| 5,932,462 A | 8/1999 | Harris | |
| 6,007,845 A | 12/1999 | Domb | |
| 6,270,806 B1 | 8/2001 | Liversidge | |
| 6,287,588 B1 | 9/2001 | Shih | |
| 6,413,539 B1 | 7/2002 | Shalaby | |
| 6,432,381 B2 | 8/2002 | Liversidge | |
| 6,495,164 B1 | 12/2002 | Ramstack | |
| 6,589,549 B2 | 7/2003 | Shih | |
| 6,706,289 B2 | 3/2004 | Lewis | |
| 8,354,476 B2 | 1/2013 | Hanes | |
| 8,409,607 B2 | 4/2013 | Hughes | |
| 8,465,778 B2 | 6/2013 | Hughes | |
| 8,481,069 B2 | 7/2013 | Hughes | |
| 8,512,738 B2 | 8/2013 | Edelman | |
| 8,628,801 B2 | 1/2014 | Garreta | |
| 8,632,809 B2 | 1/2014 | Asgharian | |
| 8,663,674 B2 | 3/2014 | Wen | |
| 8,889,193 B2 | 11/2014 | McDonnell | |
| 8,911,768 B2 | 12/2014 | Whitcup | |
| 8,957,034 B2 | 2/2015 | Hanes | |
| 8,962,577 B2 | 2/2015 | Hanes | |
| 9,056,057 B2 | 6/2015 | Popov | |
| 2002/0035264 A1 | 3/2002 | Kararli | |
| 2003/0147944 A1 * | 8/2003 | Mayer | A61K 9/1271 424/450 |
| 2003/0203038 A1 * | 10/2003 | Vail | A61K 9/1271 424/490 |
| 2004/0234611 A1 | 11/2004 | Ahlheim | |
| 2005/0009910 A1 | 1/2005 | Hughes | |
| 2005/0059881 A1 | 3/2005 | Balaban | |
| 2007/0071756 A1 | 3/2007 | Peyman | |
| 2007/0093461 A1 | 4/2007 | Shafiee | |
| 2007/0141143 A1 | 6/2007 | Smithey | |
| 2007/0149593 A1 | 6/2007 | Ghosh | |
| 2007/0231360 A1 | 10/2007 | Peyman | |
| 2007/0249536 A1 | 10/2007 | Ma | |
| 2008/0086199 A1 | 4/2008 | Dave | |
| 2008/0166411 A1 | 7/2008 | Shah | |
| 2008/0213352 A1 * | 9/2008 | Lenk | A61K 8/0208 424/450 |
| 2008/0305172 A1 | 12/2008 | Ahlheim | |
| 2009/0169611 A1 * | 7/2009 | Albrecht | A61K 9/1271 424/450 |
| 2009/0203709 A1 | 8/2009 | Steinberg | |
| 2009/0247604 A1 | 10/2009 | Tang | |
| 2010/0063135 A1 | 3/2010 | Dande | |
| 2010/0172967 A1 * | 7/2010 | Nemoto | A61K 47/00 424/450 |
| 2010/0215580 A1 | 8/2010 | Hanes | |
| 2010/0227905 A1 | 9/2010 | Kabra | |
| 2012/0028910 A1 | 2/2012 | Combal | |
| 2012/0052041 A1 | 3/2012 | Basu | |
| 2012/0157499 A1 | 6/2012 | Hughes | |
| 2012/0269894 A1 | 10/2012 | Ahlheim | |
| 2013/0071349 A1 | 3/2013 | Robinson | |
| 2013/0108551 A1 * | 5/2013 | Langereis | A61K 9/127 424/9.3 |
| 2013/0122064 A1 | 5/2013 | Ahlheim | |
| 2013/0164343 A1 | 6/2013 | Hanes | |
| 2013/0183244 A1 | 7/2013 | Hanes | |
| 2013/0217657 A1 | 8/2013 | Lindstrom | |
| 2013/0236556 A1 | 9/2013 | Lai | |
| 2013/0272994 A1 | 10/2013 | Fu | |
| 2013/0274217 A1 | 10/2013 | Hanes | |
| 2013/0316001 A1 | 11/2013 | Popov | |
| 2013/0316006 A1 | 11/2013 | Popov | |
| 2013/0316009 A1 | 11/2013 | Popov | |
| 2013/0323313 A1 | 12/2013 | Suk | |
| 2014/0031408 A1 | 1/2014 | Edelman | |
| 2014/0107025 A1 | 4/2014 | Wirostko | |
| 2014/0178475 A1 | 6/2014 | Figueiredo | |
| 2014/0248358 A1 | 9/2014 | Figueiredo | |
| 2014/0249158 A1 | 9/2014 | Figueiredo | |
| 2014/0276482 A1 | 9/2014 | Astafieva | |
| 2014/0294986 A1 | 10/2014 | Liu | |
| 2014/0329913 A1 | 11/2014 | Hanes | |
| 2015/0044270 A1 | 2/2015 | McDonnell | |
| 2015/0086484 A1 | 3/2015 | Hanes | |
| 2015/0125539 A1 | 5/2015 | Popov | |
| 2015/0265542 A1 | 9/2015 | Popov | |
| 2015/0265543 A1 | 9/2015 | Popov | |
| 2015/0297531 A1 | 10/2015 | Ensign | |

FOREIGN PATENT DOCUMENTS

| | | |
|---|---|---|
| WO | 005055985 | 6/2005 |
| WO | 2006063249 | 6/2006 |
| WO | 2006116107 | 11/2006 |
| WO | 2007016380 | 2/2007 |
| WO | 2007084418 | 7/2007 |
| WO | 2008030557 | 3/2008 |
| WO | 2010040188 | 4/2008 |
| WO | 2010132664 | 11/2010 |
| WO | 2010143969 | 12/2010 |
| WO | 011080148 | 7/2011 |
| WO | 013110028 | 7/2013 |
| WO | 013138343 | 9/2013 |
| WO | 013138346 | 9/2013 |
| WO | 013166385 | 11/2013 |
| WO | 2013166408 | 11/2013 |
| WO | 2013166436 | 11/2013 |
| WO | 2013166498 | 11/2013 |
| WO | 2014047439 | 3/2014 |
| WO | 2004060977 | 7/2014 |

OTHER PUBLICATIONS

Dong, et al., "Vascular cell-adhesion molecule-1 plays a central role in he proangiogenic effects of oxidative stress", PNAS, 108(35):14614-9 (2011).
Veronese, et al., "PEG-doxorubicin conjugates: influence of polymer structure on drug release, in vitro cytotoxicity, biodistribution, and antitumor activity", Bioconjig Chem., 16 (4):775-84 (2005).
Yokoyama, et al., "Characterization and anticancer activity of the micelle-forming polymeric anticancer drug adriamycin-conjugated poly(ethylene glycol)-poly(aspartic acid) block copolymer", Cancer Res., 50:1693-1700 (1990).
Cattel, et al., "From conventional to stealth liposomes a new frontier in cancer chemotherapy", Tumori, 83(3):237-49 (2003).
Garbuzenko, et al., "Effect of grafted PEG on liposome size and on compressibility and packing of lipid bilayer", Chem Phys Lipids, 135:117-29 (2005).
Immordino, et al., "Stealth liposomes: review of the basic science, rationale, and clinical applications, existing and potential", Int J Naomed., 1(3):297-315 (2006).

(56) References Cited

OTHER PUBLICATIONS

Ludwig, The use of mucoadhesive polymers in ocular drug delivery, Adv Drug Deliv Rev., 57:1595-639 (2005).

Memon, et al., "Optimization of formulation parameters on ocular loteprednol etabonate nanosuspension by media milling method", Int J Pharmacrut. Biol. Arch., 4:46-51 (2012).

Sahib, et al., "Solubilization of beclomethasone dipropionate in sterically stabilized phospholipid nanomicelles (SSMs):physicochemical and in vitro evaluations", Drug Des Dev Ther., 6:29-42 (2012).

Yang, et al., "Production of virus-mimetic mucus-penetrating particles for drug and gene delivery in mucosal tissues", Annual Meeting of AICHE Science and Engineering Forum, Nov. 16-21, Abstract 705B (2008).

* cited by examiner

LIPID-BASED DRUG CARRIERS FOR RAPID PENETRATION THROUGH MUCUS LININGS

CROSS REFERENCE TO RELATED APPLICATIONS

This application is a 371 application of International Application No. PCT/US2013/039731, filed May 6, 2013, which claims the benefit of and priority to U.S. U.S. Ser. No. 61/642,776 entitled "Lipid-Based Drug Carriers for Rapid Penetration Through Mucus Linings" filed May 4, 2012.

STATEMENT REGARDING FEDERALLY SPONSORED RESEARCH OR DEVELOPMENT

This invention was made with government support under grant no. EB015031 awarded by the National Institutes of Health. The government has certain rights in the invention.

FIELD OF THE INVENTION

This invention is in the field of liposomal nanoparticles for drug delivery, particularly mucus-penetrating liposomal nanoparticles.

BACKGROUND OF THE INVENTION

Mucus is a viscous and adhesive substance that efficiently traps and removes pathogens, hazard particles, and conventional drug or gene carriers from mucosal surfaces, including those that cover the female reproductive tract, GI tract, lung, airway and eyes. To deliver therapeutics efficiently across the mucosal surfaces, drug or gene carriers must be able to penetrate the mucus barrier to avoid the mucus-induced aggregation and rapid clearance.

Different strategies have been proposed to render drug or gene carriers muco-inert by covalently or non-covalently modifying particle surfaces with a dense coating of low molecular weight (MW) poly(ethylene glycol) (PEG), a hydrophilic, neutrally charged molecule that efficiently shields particles from strong adhesion to mucus. Prior formulations of mucus-penetrating particles (MPP) are mainly based on biodegradable polymers, of which the hydrophobic segment serves as the loading vehicle for poorly soluble drugs. However, it remains challenging to encapsulate water soluble agents (e.g, proteins such as antibodies or growth factors) in hydrophobic polymeric particles, especially for those with small sizes at sub-micron scale such as MPP.

Lipid-based systems, such as liposomes, have been studied as means for effective drug delivery, particularly for hydrophilic or water-soluble agents. However, these systems are generally unable to achieve efficient transmucosal delivery mainly due to the strong hindrance by the mucus mesh. The intense interactions between delivery particles and mucus constituents might also induce unwanted decomposition of the particles or the encapsulated payloads.

There exists a need for a drug delivery systems which can rapidly penetrate mucus which overcomes the limitations discussed above associated with polymeric systems.

Therefore, there is a need to provide a drug delivery system, particularly a lipid-based system, such as liposomes, which can rapidly penetrate mucus which overcomes the limitations discussed above associated with polymeric systems and methods of making and using thereof.

SUMMARY OF THE INVENTION

Mucus-penetrating liposomal nanoparticles and methods of making and using thereof are described herein. The nanoparticles contain one or more lipids, one or more PEG-conjugated lipids, and optionally one or more additional materials that physically and/or chemically stabilize the particles. The concentration of the PEG-conjugated lipid is from about 8 mole percent to about 30 mole percent. The liposomes can be prepared by any means known in the art. The nanoparticle have an average diameter of about 100 nm to about 300 nm, preferably from about 100 nm to about 250 nm, more preferably from about 100 nm to about 200 nm. The particles are mobile in mucus. "Mobile" as used herein means particles which travel a distance of at least over 10 times its radius (about 100 nm) in a 20 second movie, which corresponds to about 0.1 $\mu m^2$/sec.

The liposomes can further contain one or more therapeutic, prophylactic, and/or diagnostic agent to be delivered to a mucosal surface, such as the CV tract, the colon, the nose, the lungs, and/or the eyes. The liposomes can further contain one or more CEST agents to allow real time imaging of the particles in a live animal. The particles may also further contain an imaging agent, such as a fluorescent label. Finally, the particle may contain a mucus-disrupting agent. The particles may contain one or more of the agents listed above.

The liposomes can be combined with one or more pharmaceutically acceptable excipients to prepare pharmaceutical formulations. The liposomes can be administered by a variety of routes of administration, such as enteral or parenteral, as well as topical or pulmonary.

DETAILED DESCRIPTION OF THE INVENTION

I. Definitions

Figure 1:
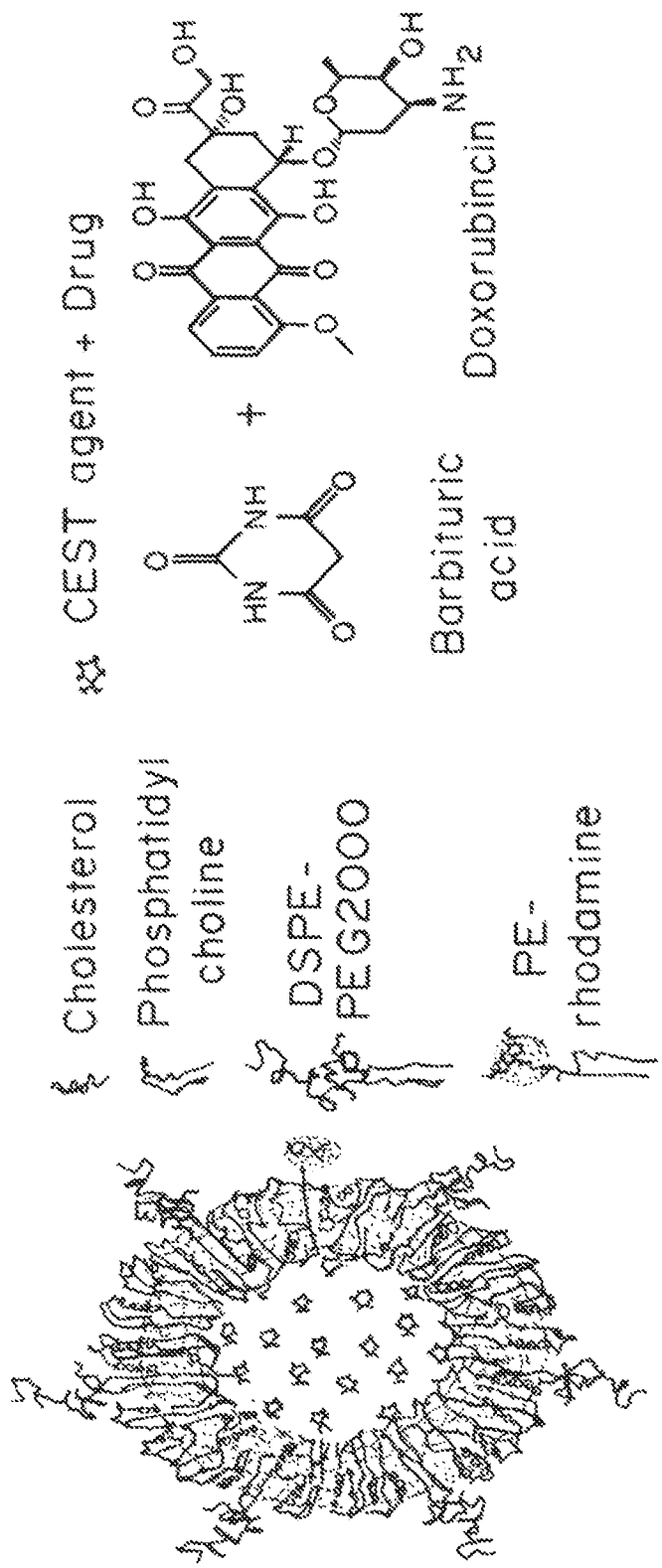
FIG. 1 is a schematic of mucus-penetrating liposomal nanoparticles formed from phosphatidyl choline (PC), PEG2000-DSPE, cholesterol, and Rhodamine-PE having encapsulated therein a CEST agent (barbituric acid) and doxorubicin.

"Liposome", as used herein, refers to vesicles or particles which possess a lipid bilayer enclosing an aqueous compartment.

"Nanoparticle," as used herein, generally refers to a particle of any shape having an average diameter from about 1 nm up to, but not including, about 1 micron, preferably from about 5 nm to about 500 nm, most preferably from about 5 nm to about 300 nm. In some embodiments, the particles have an average diameter from about 100 nm to about 300 nm, preferably from about 100 nm to about 250 nm, more preferably from about 100 nm to about 200 nm. Nanoparticles having a spherical shape are generally referred to as "nanospheres".

"Mean particle size," as used herein, generally refers to the statistical mean particle size (diameter) of the particles in a population of particles. The diameter of an essentially spherical particle may be referred to as the physical or hydrodynamic diameter. The diameter of a non-spherical particle may refer preferentially to the hydrodynamic diameter. As used herein, the diameter of a non-spherical particle may refer to the largest linear distance between two points on the surface of the particle. Mean particle size can be measured using methods known in the art, such as dynamic light scattering.

"Monodisperse" and "homogeneous size distribution," are used interchangeably herein and describe a plurality of liposomal nanoparticles or microparticles where the particles have the same or nearly the same diameter or aerodynamic diameter. As used herein, a monodisperse distribution refers to particle distributions in which 75, 76, 77, 78, 79, 80, 81, 82, 83, 84, 85, 86, 86, 88, 89, 90, 91, 92, 93, 94, 95% or greater of the distribution lies within 85, 80, 75, 70, 65, 60, 55, 50, 45, 40, 35, 30, 25, 20, 15, or 10% of the mass median diameter or aerodynamic diameter.

"Mobile" as used herein means particles which travel a distance of at least over 10 times its radius (about 100 nm) in a 20 second movie, which corresponds to about 0.1 µm²/sec.

"Hydrophilic" as used herein refers to substances that have strongly polar groups that readily interact with water.

"Lipophilic" refers to compounds having an affinity for lipids.

"Amphiphilic" refers to a molecule combining hydrophilic and lipophilic (hydrophobic) properties "Hydrophobic" as used herein refers to substances that lack an affinity for water; tending to repel and not absorb water as well as not dissolve in or mix with water.

"Pharmaceutically acceptable," as used herein, refers to compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the Food and Drug Administration.

"Biocompatible" as used herein, generally refer to materials that are, along with any metabolites or degradation products thereof, generally nontoxic to the recipient, and do not cause any significant adverse effects to the recipient. Generally speaking, biocompatible materials are materials which do not elicit a significant inflammatory or immune response when administered to a patient.

"Molecular weight," as used herein, generally refers to the relative average chain length of the bulk polymer, unless otherwise specified. In practice, molecular weight can be estimated or characterized using various methods including gel permeation chromatography (GPC) or capillary viscometry. GPC molecular weights are reported as the weight-average molecular weight (Mw) as opposed to the number-average molecular weight (Mn). Capillary viscometry provides estimates of molecular weight as the inherent viscosity determined from a dilute polymer solution using a particular set of concentration, temperature, and solvent conditions.

"Mucus," as used herein, refers to a viscoelastic natural substance containing primarily mucin glycoproteins and other materials, which protects epithelial surface of various organs/tissues, including respiratory, nasal, cervicovaginal, gastrointestinal, rectal, visual and auditory systems. "Sputum," as used herein, refers to highly viscoelastic mucus secretions consist of a variety of macromolecules such as DNA, actins and other cell debris released from dead cells in addition to mucin glycoproteins. "Sputum" is generally present in the pathogenic airways of patients afflicted by obstructive lung diseases, including but not limited to, asthma, COPD and CF. "CF mucus" and "CF sputum," as used herein, refer to mucus and sputum, respectively, from a patient suffering from cystic fibrosis. In some embodiments, the mucus is non-ovulatory human cervicovaginal mucus (CVM).

"Mucus Degrading Agent," as used herein, refers to a substance which increases the rate of mucus clearance when administered to a patient. Mucus degrading agents are known in the art. See, for example, Hanes, J. et al. Gene Delivery to the Lung. in Pharmaceutical Inhalation Aerosol Technology, Marcel Dekker, Inc., New York: 489-539 (2003). Examples of mucus degrading agents include N-acetylcysteine (NAC), which cleaves disulfide and sulfhydryl bonds present in mucin. Other mucus degrading agents include mugwort, bromelain, papain, clerodendrum, acetylcysteine, bromhexine, carbocisteine, eprazinone, mesna, ambroxol, sobrerol, domiodol, denufosol, letosteine, stepronin, tiopronin, gelsolin, thymosin β4, neltenexine, erdosteine, and various DNases including rhDNase.

The term "surfactant" as used herein refers to an agent that lowers the surface tension of a liquid.

The term "therapeutic agent" refers to an agent that can be administered to prevent or treat a disease or disorder. Therapeutic agents can be a nucleic acid, a nucleic acid analog, a small molecule, a peptidomimetic, a protein, peptide, carbohydrate or sugar, lipid, or surfactant, or a combination thereof.

The term "treating" or preventing a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease or condition includes ameliorating at least one symptom of the particular disease or condition, even if the underlying pathophysiology is not affected, such as treating the pain of a subject by administration of an analgesic agent even though such agent does not treat the cause of the pain.

The term "targeting moiety" as used herein refers to a moiety that localizes to or away from a specific locale. The moiety may be, for example, a protein, nucleic acid, nucleic acid analog, carbohydrate, or small molecule. The entity may be, for example, a therapeutic compound such as a small molecule, or a diagnostic entity such as a detectable label. The locale may be a tissue, a particular cell type, or a subcellular compartment. In one embodiment, the targeting moiety directs the localization of an active entity. The active entity may be a small molecule, protein, polymer, or metal. The active entity may be useful for therapeutic, prophylactic, or diagnostic purposes.

The term "therapeutically effective amount" refers to an amount of the therapeutic agent that, when incorporated into and/or onto particles described herein, produces some desired effect at a reasonable benefit/risk ratio applicable to any medical treatment. The effective amount may vary depending on such factors as the disease or condition being treated, the particular targeted constructs being administered, the size of the subject, or the severity of the disease or condition. One of ordinary skill in the art may empirically determine the effective amount of a particular compound without necessitating undue experimentation.

The terms "incorporated" and "encapsulated" refers to incorporating, formulating, or otherwise including an active agent into and/or onto a composition that allows for release, such as sustained release, of such agent in the desired application. The terms contemplate any manner by which a therapeutic agent or other material is incorporated into a polymer matrix, including, for example: attached to a monomer of such polymer (by covalent, ionic, or other binding interaction), physical admixture, enveloping the agent in a coating layer of polymer, incorporated into the polymer, distributed throughout the polymeric matrix, appended to the surface of the polymeric matrix (by covalent or other binding interactions), encapsulated inside the polymeric matrix, etc. The term "co-incorporation" or "co-encapsulation" refers to-the incorporation of a therapeutic agent or other material and at least one other therapeutic agent or other material in a subject composition.

II. Mucus-Penetrating Liposomal Particles

Mucus-penetrating liposomal particles are described herein. A liposome is a synthetic vesicle or particle containing a lipid bilayer. Liposomes can be used for drug delivery. The major types of liposomes are the multilamellar vesicle (MLV), the small unilamellar vesicle (SUV), the large unilamellar vesicle (LUV), and the cochleate vesicle.

Liposomes have been pegylated, e.g., prepared from PEG-conjugated lipids, to prepare stealth liposomes for intravenous administration. The PEG extends the blood circulation time which reduces mononuclear phagocyte system uptake, i.e., stealth liposomes. Such liposomes typically contain about 3-7 mole percent PEG-conjugated lipids. In contrast, the liposomes described herein are mucus penetrating. It has been found that significantly higher concentrations of PEG-conjugated lipids are necessary to impart mucus-penetrating properties. The concentration of PEG-conjugated lipids is typically at least about 8 or about 10 mole percent, for example from about 8 or about 10 to about 30 mole percent, preferably from about 8 or about 10 mole percent to about 20 mole percent.

A. Lipids

The liposomes described herein contain one or more lipid components. Lipids are naturally occurring, synthetic, or semi-synthetic molecules that include fats, waxes, sterols, fat-soluble vitamins (such as vitamins A, D, E, and K), monoglycerides, diglycerides, triglycerides, phospholipids, and others.

Lipids may be broadly defined as hydrophobic or amphiphilic small molecules; the amphiphilic nature of some lipids allows them to form structures such as vesicles, liposomes, or membranes in an aqueous environment. Biological lipids originate entirely or in part from two distinct types of biochemical subunits or "building-blocks": ketoacyl and isoprene groups.

Using this approach, lipids may be divided into eight categories: fatty acids, glycerolipids, glycerophospholipids, sphingolipids, saccharolipids, and polyketides (derived from condensation of ketoacyl subunits); and sterol lipids and prenol lipids (derived from condensation of isoprene subunits).

The concentration of the lipid is from about 25 to 99 mole percent, preferably about 25 to about 95 mole percent, more preferably from about 20 to about 90 mole percent, most preferably from about 20 to about 80 mole percent. In some embodiments, the concentration may be from about 40 to about 70 mole percent, preferably from about 40 to about 60 mole percent.

1. Fatty Acids

Fatty acids, or fatty acid residues when they form part of a lipid, are a diverse group of molecules which can be prepared synthetically or synthesized naturally by chain-elongation of an acetyl-CoA primer with malonyl-CoA or methylmalonyl-CoA groups in a process called fatty acid synthesis. Fatty acids are made of a hydrocarbon chain that terminates with a carboxylic acid group; this arrangement confers the molecule with a polar, hydrophilic end, and a nonpolar, hydrophobic end that is insoluble in water. The carbon chain, typically between four and 24 carbons long, may be saturated or unsaturated, and may be attached to functional groups containing oxygen, halogens, nitrogen, and sulfur. Where a double bond exists, there is the possibility of either a cis or trans geometric isomerism, which significantly affects the molecule's configuration. Cis-double bonds cause the fatty acid chain to bend, an effect that is compounded with more double bonds in the chain. Most naturally occurring fatty acids are of the cis configuration, although the trans form does exist in some natural and partially hydrogenated fats and oils. Other major lipid classes in the fatty acid category are the fatty esters and fatty amides.

2. Glycerolipids

Glycerolipids are composed mainly of mono-, di-, and tri-substituted glycerols, the most well-known being the fatty acid triesters of glycerol, called triglycerides. The word "triacylglycerol" is sometimes used synonymously with "triglyceride", though the latter lipids contain no hydroxyl group. In these compounds, the three hydroxyl groups of glycerol are each esterified, typically by different fatty acids.

Additional subclasses of glycerolipids are represented by glycosylglycerols, which are characterized by the presence of one or more sugar residues attached to glycerol via a glycosidic linkage. Examples of structures in this category are the digalactosyldiacylglycerols found in plant membranes and seminolipid from mammalian sperm cells.

3. Glycerophospholipids

Glycerophospholipids, usually referred to as phospholipids, are ubiquitous in nature and are key components of the lipid bilayer of cells, as well as being involved in metabolism and cell signaling. Most phospholipids contain a diglyceride, a phosphate group, and a simple organic molecule such as choline; one exception to this rule is sphingomyelin, which is derived from sphingosine instead of glycerol.

The structure of the phospholipid molecule generally consists of hydrophobic tails and a hydrophilic head. The 'head' is attracted to water, while the hydrophobic 'tails' are repelled by water and are forced to aggregate. The hydrophilic head contains the negatively charged phosphate group, and may contain other polar groups. The hydrophobic tail usually consists of long fatty acid hydrocarbon chains. When placed in water, phospholipids form a variety of structures depending on the specific properties of the phospholipid. Lipid bilayers occur when hydrophobic tails line up against one another, forming a membrane of hydrophilic heads on both sides facing the water.

Glycerophospholipids may be subdivided into distinct classes, based on the nature of the polar headgroup at the sn-3 position of the glycerol backbone in eukaryotes and eubacteria, or the sn-1 position in the case of archaebacteria. Examples of glycerophospholipids found in biological membranes are phosphatidylcholine (also known as PC, GPCho or lecithin), phosphatidylethanolamine (PE or GPEtn) and phosphatidylserine (PS or GPSer).

In eukaryotes, phospholipids are generally classified into two types: diacylglycerides and phosphingolipids. Examples of diacylglycerides include, but are not limited to, phosphatidic acid (phosphatidate) (PA), phosphatidylethanolamine (cephalin) (PE), phosphatidylcholine (lecithin) (PC), phosphatidylserine (PS), and phosphoinositides, such as phosphatidylinositol (PI), phosphatidylinositol phosphate (PIP), phosphatidylinositol bisphosphate (PIP2) and, phosphatidylinositol triphosphate (PIP3). Examples of phospingolipids include, but are not limited to, ceramide phosphorylcholine (Sphingomyelin) (SPH), ceramide phosphorylethanolamine (Sphingomyelin) (Cer-PE), and Ceramide phosphoryllipid.

Other phospholipids that can be used are shown in Table 1 below.

TABLE 1

| Phospholipids | | | |
|---|---|---|---|
| Abbreviation | CAS No. | Name | Type |
| DDPC | 3436-44-0 | 1,2-Didecanoyl-sn-glycero-3-phosphocholine | Phosphatidylcholine |
| DEPA-NA | 80724-31-8 | 1,2-Dierucoyl-sn-glycero-3-phosphate (Sodium Salt) | Phosphatidic acid |
| DEPC | 56649-39-9 | 1,2-Dierucoyl-sn-glycero-3-phosphocholine | Phosphatidylcholine |
| DEPE | 988-07-2 | 1,2-Dierucoyl-sn-glycero-3-phosphoethanolamine | Phosphatidylethanolamine |
| DEPG-NA | | 1,2-Dierucoyl-sn-glycero-3[Phospho-rac-(1-glycerol . . . ) (Sodium Salt) | Phosphatidylglycerol |
| DLOPC | 998-06-1 | 1,2-Dilinoleoyl-sn-glycero-3-phosphocholine | Phosphatidylcholine |
| DLPA-NA | | 1,2-Dilauroyl-sn-glycero-3-phosphate (Sodium Salt) | Phosphatidic acid |
| DLPC | 18194-25-7 | 1,2-Dilauroyl-sn-glycero-3-phosphocholine | Phosphatidylcholine |
| DLPE | | 1,2-Dilauroyl-sn-glycero-3-phosphoethanolamine | Phosphatidylethanolamine |
| DLPG-NA | | 1,2-Dilauroyl-sn-glycero-3[Phospho-rac-(1-glycerol . . . ) (Sodium Salt) | Phosphatidylglycerol |
| DLPG-NH4 | | 1,2-Dilauroyl-sn-glycero-3[Phospho-rac-(1-glycerol . . . ) (Ammonium Salt) | |
| DLPS-NA | | 1,2-Dilauroyl-sn-glycero-3-phosphoserine (Sodium Salt) | Phosphatidylserine |
| DMPA-NA | 80724-3 | 1,2-Dimyristoyl-sn-glycero-3-phosphate (Sodium Salt) | Phosphatidic acid |
| DMPC | 18194-24-6 | 1,2-Dimyristoyl-sn-glycero-3-phosphocholine | Phosphatidylcholine |
| DMPE | 988-07-2 | 1,2-Dimyristoyl-sn-glycero-3-phosphoethanolamine | Phosphatidylethanolamine |
| DMPG-NA | 67232-80-8 | 1,2-Dimyristoyl-sn-glycero-3[Phospho-rac-(1-glycerol . . . ) (Sodium Salt) | Phosphatidylglycerol |
| DMPG-NH4 | | 1,2-Dimyristoyl-sn-glycero-3[Phospho-rac-(1-glycerol . . . ) (Ammonium Salt) | Phosphatidylglycerol |
| DMPG-NH4/NA | | 1,2-Dimyristoyl-sn-glycero-3[Phospho-rac-(1-glycerol . . . ) (Sodium/Ammonium Salt) | Phosphatidylglycerol |
| DMPS-NA | | 1,2-Dimyristoyl-sn-glycero-3-phosphoserine (Sodium Salt) | Phosphatidylserine |
| DOPA-NA | | 1,2-Dioleoyl-sn-glycero-3-phosphate (Sodium Salt) | Phosphatidic acid |
| DOPC | 4235-95-4 | 1,2-Dioleoyl-sn-glycero-3-phosphocholine | Phosphatidylcholine |
| DOPE | 4004-5-1- | 1,2-Dioleoyl-sn-glycero-3-phosphoethanolamine | Phosphatidylethanolamine |
| DOPG-NA | 62700-69-0 | 1,2-Dioleoyl-sn-glycero-3[Phospho-rac-(1-glycerol . . . ) (Sodium Salt) | Phosphatidylglycerol |
| DOPS-NA | 70614-14-1 | 1,2-Dioleoyl-sn-glycero-3-phosphoserine (Sodium Salt) | Phosphatidylserine |
| DPPA-NA | 71065-87-7 | 1,2-Dipalmitoyl-sn-glycero-3-phosphate (Sodium Salt) | Phosphatidic acid |
| DPPC | 63-89-8 | 1,2-Dipalmitoyl-sn-glycero-3-phosphocholine | Phosphatidylcholine |
| DPPE | 923-61-5 | 1,2-Dipalmitoyl-sn-glycero-3-phosphoethanolamine | Phosphatidylethanolamine |
| DPPG-NA | 67232-81-9 | 1,2-Dipalmitoyl-sn-glycero-3[Phospho-rac-(1-glycerol. . . ) (Sodium Salt) | Phosphatidylglycerol |
| DPPG-NH4 | 73548-70-6 | 1,2-Dipalmitoyl-sn-glycero-3[Phospho-rac-(1-glycerol . . . ) (Ammonium Salt) | Phosphatidylglycerol |
| DPPS-NA | | 1,2-Dipalmitoyl-sn-glycero-3-phosphoserine (Sodium Salt) | Phosphatidylserine |
| DSPA-NA | 108321-18-2 | 1,2-Distearoyl-sn-glycero-3-phosphate (Sodium Salt) | Phosphatidic acid |
| DSPC | 816-94-4 | 1,2-Distearoyl-sn-glycero-3-phosphocholine | Phosphatidylcholine |
| DSPE | 1069-79-0 | 1,2-Distearoyl-sn-glycero-3-phosphoethanolamine | Phosphatidylethanolamine |
| DSPG-NA | 67232-82-0 | 1,2-Distearoyl-sn-glycero-3[Phospho-rac-(1-glycerol . . . ) (Sodium Salt) | Phosphatidylglycerol |
| DSPG-NH4 | 108347-80-4 | 1,2-Distearoyl-sn-glycero-3[Phospho-rac-(1-glycerol . . . ) (Ammonium Salt) | Phosphatidylglycerol |

TABLE 1-continued

Phospholipids

| Abbreviation | CAS No. | Name | Type |
|---|---|---|---|
| DSPS-NA | | 1,2-Distearoyl-sn-glycero-3-Phosphatidylserine phosphoserine (Sodium Salt) | |
| Egg Sphingomyelin empty Liposome | | | |
| EPC | | Egg-PC | Phosphatidylcholine |
| HEPC | | Hydrogenated Egg PC High purity | Phosphatidylcholine |
| HSPC | | Hydrogenated Soy PC | Phosphatidylcholine |
| HSPC | | Hydrogenated Soy PC | Phosphatidylcholine |
| LYSOPC MYRISTIC | 18194-24-6 | 1-Myristoyl-sn-glycero-3-phosphocholine | Lysophosphatidylcholine |
| LYSOPC PALMITIC | 17364-16-8 | 1-Palmitoyl-sn-glycero-3-phosphocholine | Lysophosphatidylcholine |
| LYSOPC STEARIC | 19420-57-6 | 1-Stearoyl-sn-glycero-3-phosphocholine | Lysophosphatidylcholine |
| Milk Sphingomyelin | | | |
| MPPC | | 1-Myristoyl-2-palmitoyl-sn-glycero 3-phosphocholine | Phosphatidylcholine |
| MSPC | | 1-Myristoyl-2-stearoyl-sn-glycero-3 phosphocholine | Phosphatidylcholine |
| PMPC | | 1-Palmitoyl-2-myristoyl-sn-glycero-3 phosphocholine | Phosphatidylcholine |
| POPC | 26853-31-6 | 1-Palmitoyl-2-oleoyl-sn-glycero-3-phosphocholine | Phosphatidylcholine |
| POPE | | 1-Palmitoyl-2-oleoyl-sn-glycero-3-phosphoethanolamine | Phosphatidylethanolamine |
| POPG-NA | 81490-05-3 | 1-Palmitoyl-2-oleoyl-sn-glycero-3[Phospho-rac-(1-glycerol) . . . ] (Sodium Salt) | Phosphatidylglycerol |
| PSPC | | 1-Palmitoyl-2-stearoyl-sn-glycero-3 phosphocholine | Phosphatidylcholine |
| SMPC | | 1-Stearoyl-2-myristoyl-sn-glycero-3 phosphocholine | Phosphatidylcholine |
| SOPC | | 1-Stearoyl-2-oleoyl-sn-glycero-3-phosphocholine | Phosphatidylcholine |
| SPPC | | 1-Stearoyl-2-palmitoyl-sn-glycero-3-phosphocholine | Phosphatidylcholin |

In some embodiments, the lipid component is one or more phospholipids. In some embodiments, the lipid is, or contains, phosphatidylcholine (PC, e.g., egg PC or hydrogenated soy PC). The concentration of the phospholipid is from about 25 to 99 mole percent, preferably about 25 to about 95 mole percent, more preferably from about 20 to about 90 mole percent, most preferably from about 20 to about 80 mole percent. In some embodiments, the concentration may be from about 40 to about 70 mole percent, preferably from about 40 to about 60 mole percent.

4. Sphingolipids

Sphingolipids are a complicated family of compounds that share a common structural feature, a sphingoid base backbone that is synthesized de novo from the amino acid serine and a long-chain fatty acyl CoA, then converted into ceramides, phosphosphingolipids, glycosphingolipids and other compounds. The major sphingoid base of mammals is commonly referred to as sphingosine. Ceramides (N-acyl-sphingoid bases) are a major subclass of sphingoid base derivatives with an amide-linked fatty acid. The fatty acids are typically saturated or mono-unsaturated with chain lengths from 16 to 26 carbon atoms.

The major phosphosphingolipids of mammals are sphingomyelins (ceramide phosphocholines), whereas insects contain mainly ceramide phosphoethanolamines and fungi have phytoceramide phosphoinositols and mannose-containing headgroups. The glycosphingolipids are a diverse family of molecules composed of one or more sugar residues linked via a glycosidic bond to the sphingoid base. Examples of these are the simple and complex glycosphingolipids such as cerebrosides and gangliosides.

5. Sterol Lipids

Sterol lipids, such as cholesterol and its derivatives, are an important component of membrane lipids, along with the glycerophospholipids and sphingomyelins. The steroids are all derived from the same fused four-ring core structure. Other examples of sterols are the bile acids and their conjugates. The plant equivalents are the phytosterols, such as β-sitosterol, stigmasterol, and brassicasterol.

6. Prenol Lipids

Prenol lipids are synthesized from the five-carbon-unit precursors isopentenyl diphosphate and dimethylallyl diphosphate. The simple isoprenoids (linear alcohols, diphosphates, etc.) are formed by the successive addition of C5 units, and are classified according to number of these terpene units. Structures containing greater than 40 carbons are known as polyterpenes. Carotenoids are important simple isoprenoids that function as antioxidants and as precursors of vitamin A. Another biologically important class of molecules is exemplified by the quinones and hydroquinones, which contain an isoprenoid tail attached to a quinonoid core of non-isoprenoid origin. Vitamin E and vitamin K, as well as the ubiquinones, are examples of this class. Prokaryotes synthesize polyprenols (called bactoprenols) in which the terminal isoprenoid unit attached to oxygen remains unsaturated, whereas in animal polyprenols (dolichols) the terminal isoprenoid is reduced.

7. Saccharolipids

Saccharolipids describe compounds in which fatty acids are linked directly to a sugar backbone, forming structures that are compatible with membrane bilayers. In the saccharolipids, a monosaccharide substitutes for the glycerol backbone present in glycerolipids and glycerophospholipids. The most familiar saccharolipids are the acylated glucosamine precursors of the Lipid A component of the lipopolysaccharides in Gram-negative bacteria. Typical lipid A molecules are disaccharides of glucosamine, which are derivatized with as many as seven fatty-acyl chains.

B. PEG-Conjugated Lipids

The liposomes also contain a PEG-conjugated lipid. The lipid can be conjugated to PEG itself or a copolymer containing PEG, such as PEO-PPO copolymer available under the tradename PLURONIC. Other materials, such as polymers, surfactants, nucleic acids, proteins, etc., can be used in place of or in combination with PEG provided the material enhances or facilitate diffusion through mucus.

The PEG-conjugated lipid can be a pegylated form of any of the lipids discussed above. In some embodiments, the PEG-conjugated lipid is a PEG-conjugated phospholipid. In particular embodiments, the PEG-conjugated phospholipid is PEG-phosphatidylethanolamine (PEG-PE). The concentration of the PEG-conjugated lipid in the liposome is at least about 10 mole percent, for example, about 10 to about 30 mole percent, preferably about 10 mole percent to about 20 mole percent.

The molecular weight of PEG can vary. In some embodiments, the molecular weight of PEG is from about 500 Daltons to about 10,000 Daltons, preferably from about 500 Daltons to about 5,000 Daltons, more preferably from about 1,000 Daltons to about 5,000 Daltons, most preferably from about 2,000 Daltons to about 4,000 Daltons. In particular embodiments, the molecular weight of PEG is about 2000 Daltons.

C. Stabilizer

The liposome can also contain one or more stabilizers. Stabilizers are components or additional components in the liposomes that reduce or prevent vesicle destabilization and/or opsonization and concomitant release of encapsulated agents or drugs. For example, stabilizers, such as cholesterol and other materials, enhance the mechanical strength of the lipid bilayer. Other materials include one or more of the lipids described above.

The concentration of the stabilizer(s) is at least about 5 mole percent, preferably at least about 10 mole percent, more preferably at least about 20 mole percent, most preferably at least about 30 mole percent. In some embodiments, the concentration of the stabilizer is from about 5 mole % to about 50 mole %. In particular embodiment, the concentration of the stabilizer is about 25, 50, or 70 mole percent. In a more particular embodiment, the concentration of the stabilizer is about 25 mole percent.

In some embodiments, the stabilizer is cholesterol and is present in a concentration as described above. Other suitable stabilizers include ganglioside $G_{M1}$. In other embodiments, the stabilizer can be the PEG-conjugated lipid and thus an additional stabilizer or stabilizers is not required.

D. Properties of Liposomal Nanoparticles

1. Surface Density of Polyethylene Glycol (PEG)

Surface density of poly(ethylene glycol) (PEG) on nanoparticles is a key parameter in determining their successful applications in-vivo. The controlled delivery of drugs to mucosal surfaces is challenging because of the presence of the protective mucus layer, and the mucus-penetrating liposomal particles show promise at improved drug distribution, retention and efficacy at mucosal surfaces. The dense coating of PEG on biodegradable liposomal nanoparticles can allow rapid penetration through mucus because of the greatly reduced adhesive interaction between mucus constituents and liposomal nanoparticles.

The concentration of PEG-conjugated lipid in discussed above with reference to the mole percent of PEG-conjugated lipid. The amount of PEG can also be described in terms of surface density. Nuclear magnetic resonance (NMR) can be used to assess the surface PEG density on PEG-containing liposomal nanoparticles described herein, both qualitatively and quantitatively (PEG peak typically observed ~3.65 ppm). In some embodiments, PEG surface density can be controlled by preparing the particles from a mixture of pegylated and non-pegylated lipids. For example, the surface density of PEG on liposomal nanoparticles can be precisely controlled by preparing particles from a mixture of PEG-conjugated lipid and non-PEG-conjugated lipid. Quantitative $^1$H nuclear magnetic resonance (NMR) can be used to measure the surface PEG density on liposomal nanoparticles. Multiple particle tracking in human mucus and the study of mucin binding and tissue distribution in mouse vagina revealed that there exists a PEG density threshold, which is approximately 10-20 mole percent, for the liposomal nanoparticles to be effective in penetrating mucus. This density threshold may vary depending on a variety of factors including the lipid or lipids used to prepare the particles, particle size, and/or molecular weight of PEG.

The density of the coating can be varied based on a variety of factors including the surface altering material and the composition of the particle. In one embodiment, the density of the surface altering material, such as PEG, as measured by $^1$H NMR is at least, 0.1, 0.2, 0.5, 0.8, 1, 2, 5, 8, 10, 15, 20, 25, 40, 50, 60, 75, 80, 90, or 100 chains per nm$^2$. The range above is inclusive of all values from 0.1 to 100 units per nm$^2$. In particular embodiments, the density of the surface altering material, such as PEG, is from about 1 to about 25 chains/nm$^2$, from about 1 to about 20 chains/nm$^2$, from about 5 to about 20 chains/nm$^2$, from about 5 to about 18 chains/nm$^2$, from about 5 to about 15 chains/nm$^2$, or from about 10 to about 15 chains/nm$^2$. The concentration of the surface altering material, such as PEG, can also be varied. In particular embodiments, the density of the surface-altering material (e.g., PEG) is such that the surface-altering material (e.g. PEG) adopted an extended brush configuration. In other embodiments, the mass of the surface-altering moiety is at least 1/10,000, 1/7500, 1/5000, 1/4000, 1/3400, 1/2500, 1/2000, 1/1500, 1/1000, 1/750, 1/500, 1/250, 1/200, 1/150, 1/100, 1/75, 1/50, 1/25, 1/20, 1/5, 1/2, or 9/10 of the mass of the particle. The range above is inclusive of all vales from 1/10,000 to 9/10.

2. Ability to Penetrate Mucus

The liposomal nanoparticles described herein exhibit enhanced transport through mucus, such as non-ovulatory human cervicovaginal mucus (CVM). In some embodiments, the liposomal nanoparticles travel through mucus, such as human cervicovaginal mucus, at certain absolute diffusivities. In certain embodiments, the particles may travel at diffusivities of at least $1\times10^4$, $2\times10^4$, $5\times10^4$, $1\times10^3$, $2\times10^3$, $5\times10^3$, $1\times10^2$, $2\times10^2$, $4\times10^2$, $5\times10^2$, $6\times10^2$, $8\times10^2$, $1\times10^1$, $2\times10^1$, $5\times10^1$, 2, 1, 0.9, 0.8, 0.7, 0.6, 0.5, 0.4, 0.3, 0.2, or 0.1 µm$^2$/s at a time scale of 1 s. In contrast, non-penetrating particles have a diffusivity of at least about $1\times10^{-4}$ µm$^2$/s.

The ability of the particles to diffuse through mucus can also be evaluated qualitatively by visual inspection. In some embodiments, the concentration of PEG is about 10 mole percent and at least 50, 60, 70, 80, or 90% of the particles are mobile in non-ovulatory CVM at 2 hours and at least 30, 40, 50, 60, or 70% of the particles are mobile in non-ovulatory CVM at 15 hours. The particles exhibit little or no aggregation. In other embodiments, the concentration of PEG-conjugated lipid is about 20% and at least about 75, 80, 85, 90, 95, 96, 96, 98, or 99% of the particles are mobile in non-ovulatory CVM at 2 hours and at least about 80, 85, 86, 87, 88, 89, 90, 91, 92, 93, 94, 95, 96, 97, 98, or 99% of the particles are mobile in non-ovulatory CVM at 15 hours. The particles are well dispersed with little or no aggregation.

In certain embodiments, the particles comprising a surface-altering agent that inhibits the adsorption of fluorescently labeled avidin, wherein the particle adsorbs less than 99%, 95%, 90%, 70%, 50%, 40%, 30%, 20%, 15%, 10%, 8%, 6%, 5%, 4%, 3%, 2%, 1%, 0.5%, 0.1%, 0.05%, or 0.01% of the amount of fluorescently labeled avidin that is adsorbed by a corresponding particle lacking the surface-altering agent, as calculated by average maximum fluorescent intensity.

In certain embodiments, the particles contain a surface-altering agent that affects the zeta-potential of the particle, wherein the zeta potential of said particle is between −100 mv and 10 mv, between −50 mv and 10 mv, between −25 mv and 10 mv, between −20 mv and 5 mv, between −10 mv and 10 mv, between −10 mv and 5 mv, between −5 mv and 5 mv, or even between −2 mv and 2 mv.

3. Stability

The mucus-penetrating liposomal nanoparticles are physically and chemically stable. "Physically stable", as used herein, means that the particle size and/or polydispersity remain constant over an extended period of time.

In some embodiments, "physically stable" means the change in the average diameter of the particle is less than 10, 9, 8, 7, 6, 5, 4, 3, 2, or 1% over, 2, 4, 6, 8, 12, 16, 20, 24, 30, 36, or 48 hours. In particular embodiments, the change in the average diameter of the particles is less than 10, 9, 8, 7, 6, 5, 4, 3, or 2% after 48 hours.

In other embodiments, "physically stable" means the change in the polydispersity of the particle is less than 10, 9, 8, 7, 6, 5, 4, 3, 2, or 1% over, 2, 4, 6, 8, 12, 16, 20, 24, 30, 36, or 48 hours. In particular embodiments, the change in the polydispersity of the particles is less than 10, 9, 8, 7, 6, 5, 4, 3, 2 or 1% after 48 hours.

The particles preferably show little or no aggregation, remaining well dispersed when introduced into mucus.

E. Therapeutic, Prophylactic, and/or Diagnostic Agents

1. Therapeutic Agents

In some embodiments, the particles have encapsulated therein, dispersed therein, and/or covalently or non-covalently associate with the surface one or more therapeutic agents. The therapeutic agent can be a small molecule, protein, polysaccharide or saccharide, nucleic acid molecule and/or lipid. In some embodiments, the agent or agents are hydrophilic or water-soluble.

i. Small Molecule Therapeutic Agents

Exemplary classes of small molecule therapeutic agents include, but are not limited to, analgesics, anti-inflammatory drugs, antipyretics, antidepressants, antiepileptics, antipsychotic agents, neuroprotective agents, anti-proliferatives, such as anti-cancer agent, anti-infectious agents, such as antibacterial agents and antifungal agents, antihistamines, antimigraine drugs, antimuscarinics, anxioltyics, sedatives, hypnotics, antipsychotics, bronchodilators, anti-asthma drugs, cardiovascular drugs, corticosteroids, dopaminergics, electrolytes, gastro-intestinal drugs, muscle relaxants, nutritional agents, vitamins, parasympathomimetics, stimulants, anorectics and anti-narcoleptics. Nutraceuticals can also be incorporated. These may be vitamins, supplements such as calcium or biotin, or natural ingredients such as plant extracts or phytohormones.

In one embodiment, the liposomes contain an anti-tumor agent. Classes of antitumor agents include, but are not limited to, angiogenesis inhibitors, DNA intercalators/cross-linkers, DNA synthesis inhibitors, DNA-RNA transcription regulators, enzyme inhibitors, gene regulators, microtubule inhibitors, and other antitumor agents.

Examples of angiogenesis inhibitors include, but are not limited to, Angiostatin K1-3, DL-α-Difluoromethyl-ornithine, Endostatin, Fumagillin, Genistein, Minocycline, Staurosporine, (±)-Thalidomide, revlimid, and analogs and derivatives thereof.

Examples of DNA intercalators/cross-linkers include, but are not limited to, Bleomycin, Carboplatin, Carmustine, Chlorambucil, Cyclophosphamide, cis-Diammineplatinum (II) dichloride (Cisplatin), Melphalan, Mitoxantrone, Oxaliplatin, analogs and derivatives thereof.

Examples of DNA-RNA transcription regulators include, but are not limited to, Actinomycin D, Daunorubicin, Doxorubicin, Homoharringtonine, Idarubicin, and analogs and derivatives thereof.

Examples of enzyme inhibitors include, but are not limited to, S(+)-Camptothecin, Curcumin, (−)-Deguelin, 5,6-Dichlorobenz-imidazole 1-β-D-ribofuranoside, Etoposide, Formestane, Fostriecin, Hispidin, 2-Imino-1-imidazolidineacetic acid (Cyclocreatine), Mevinolin, Trichostatin A, Tyrphostin AG 34, Tyrphostin AG 879, and analogs and derivatives thereof.

Examples of gene regulators include, but are not limited to, 5-Aza-2'-deoxycytidine, 5-Azacytidine, Cholecalciferol (Vitamin D3), Hydroxytamoxifen, Melatonin, Mifepristone, Raloxifene, all trans-Retinal (Vitamin A aldehyde), Retinoic acid, all trans (Vitamin A acid), 9-cis-Retinoic Acid, 13-cis-Retinoic acid, Retinol (Vitamin A), Tamoxifen, Troglitazone, and analogs and derivative thereof.

Examples of microtubule inhibitors include, but are not limited to, Colchicine, Dolastatin 15, Nocodazole, Paclitaxel, docetaxel, Podophyllotoxin, Rhizoxin, Vinblastine, Vincristine, Vinorelbine (Navelbine), and analogs and derivatives thereof.

Examples of other antitumor agents include, but are not limited to, 17-(Allylamino)-17-demethoxygeldanamycin, 4-Amino-1,8-naphthalimide, Apigenin, Brefeldin A, Cimetidine, Dichloromethylene-diphosphonic acid, Leuprolide (Leuprorelin), Luteinizing Hormone-Releasing Hormone, Pifithrin-α, Rapamycin, Sex hormone-binding globulin, Thapsigargin, Urinary trypsin inhibitor fragment (Bikunin), and analogs and derivatives thereof.

ii. Nucleic Acids

In some embodiments, the agent is one or more nucleic acids. The nucleic acid can alter, correct, or replace an endogenous nucleic acid sequence. The nucleic acid is used to treat cancers, correct defects in genes in other pulmonary diseases and metabolic diseases affecting lung function, genes such as those for the treatment of Parkinsons and ALS where the genes reach the brain through nasal delivery.

Gene therapy is a technique for correcting defective genes responsible for disease development. Researchers may use one of several approaches for correcting faulty genes: A normal gene may be inserted into a nonspecific location within the genome to replace a nonfunctional gene. An abnormal gene can be swapped for a normal gene through homologous recombination. The abnormal gene can be repaired through selective reverse mutation, which returns the gene to its normal function. The regulation (the degree to which a gene is turned on or off) of a particular gene can be altered.

The nucleic acid can be a DNA, RNA, a chemically modified nucleic acid, or combinations thereof. For example, methods for increasing stability of nucleic acid half-life and resistance to enzymatic cleavage are known in the art, and can include one or more modifications or substitutions to the nucleobases, sugars, or linkages of the polynucleotide. The nucleic acid can be custom synthesized to contain properties that are tailored to fit a desired use. Common modifications include, but are not limited to use of locked nucleic acids (LNAs), unlocked nucleic acids (DNAs), morpholinos, peptide nucleic acids (PNA), phosphorothioate linkages, phosphonoacetate linkages, propyne analogs, 2'-O-methyl RNA, 5-Me-dC, 2'-5' linked phosphodiester linage, Chimeric Linkages (Mixed phosphorothioate and phosphodiester linkages and modifications), conjugation with lipid and peptides, and combinations thereof.

In some embodiments, the nucleic acid includes internucleotide linkage modifications such as phosphate analogs having achiral and uncharged intersubunit linkages (e.g., Sterchak, E. P. et al., *Organic Chem.*, 52:4202, (1987)), or uncharged morpholino-based polymers having achiral intersubunit linkages (see, e.g., U.S. Pat. No. 5,034,506). Some internucleotide linkage analogs include morpholidate, acetal, and polyamide-linked heterocycles. Other backbone and linkage modifications include, but are not limited to, phosphorothioates, peptide nucleic acids, tricyclo-DNA, decoy oligonucleotide, ribozymes, spiegelmers (containing L nucleic acids, an apatamer with high binding affinity), or CpG oligomers.

Phosphorothioates (or S-oligos) are a variant of normal DNA in which one of the nonbridging oxygens is replaced by a sulfur. The sulfurization of the internucleotide bond dramatically reduces the action of endo- and exonucleases including 5' to 3' and 3' to 5' DNA POL 1 exonuclease, nucleases S1 and P1, RNases, serum nucleases and snake venom phosphodiesterase. In addition, the potential for crossing the lipid bilayer increases. Because of these important improvements, phosphorothioates have found increasing application in cell regulation. Phosphorothioates are made by two principal routes: by the action of a solution of elemental sulfur in carbon disulfide on a hydrogen phosphonate, or by the more recent method of sulfurizing phosphite triesters with either tetraethylthiuram disulfide (TETD) or 3H-1, 2-bensodithiol-3-one 1, 1-dioxide (BDTD).4 The latter methods avoid the problem of elemental sulfur's insolubility in most organic solvents and the toxicity of carbon disulfide. The TETD and BDTD methods also yield higher purity phosphorothioates.

Peptide nucleic acids (PNA) are molecules in which the phosphate backbone of oligonucleotides is replaced in its entirety by repeating N-(2-aminoethyl)-glycine units and phosphodiester bonds are replaced by peptide bonds. The various heterocyclic bases are linked to the backbone by methylene carbonyl bonds. PNAs maintain spacing of heterocyclic bases that is similar to oligonucleotides, but are achiral and neutrally charged molecules. Peptide nucleic acids are typically comprised of peptide nucleic acid monomers. The heterocyclic bases can be any of the standard bases (uracil, thymine, cytosine, adenine and guanine) or any of the modified heterocyclic bases described below. A PNA can also have one or more peptide or amino acid variations and modifications. Thus, the backbone constituents of PNAs may be peptide linkages, or alternatively, they may be non-peptide linkages. Examples include acetyl caps, amino spacers such as 8-amino-3,6-dioxaoctanoic acid (referred to herein as O-linkers), and the like. Methods for the chemical assembly of PNAs are well known.

In some embodiments, the nucleic acid includes one or more chemically-modified heterocyclic bases including, but are not limited to, inosine, 5-(1-propynyl) uracil (pU), 5-(1-propynyl) cytosine (pC), 5-methylcytosine, 8-oxo-adenine, pseudocytosine, pseudoisocytosine, 5 and 2-amino-5-(2'-deoxy-β-D-ribofuranosyl)pyridine (2-aminopyridine), and various pyrrolo- and pyrazolopyrimidine derivatives, 4-acetylcytosine, 8-hydroxy-N-6-methyladenosine, aziridinylcytosine, 5-(carboxyhydroxylmethyl) uracil, 5-bromouracil, 5-carboxymethylaminomethyl-2-thiouracil, 5-carboxymethylaminomethyluracil, dihydrouracil, N6-isopentenyladenine, 1-methyladenine, 1-methylpseudouracil, 1-methyl guanine, 1-methylinosine, 2,2-dimethylguanine, 2-methyladenine, 2-methylguanine, 3-methylcytosine, N6-methyladenine, 7-methylguanine, 5-methylaminomethyluracil, 5-methoxy-aminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, 2,6-diaminopurine, and 2'-modified analogs such as, but not limited to O-methyl, amino-, and fluoro-modified analogs. Inhibitory RNAs modified with 2'-flouro (2'-F) pyrimidines appear to have favorable properties in vitro.

In some embodiments the nucleic acid includes one or more sugar moiety modifications, including, but are not limited to, 2'-O-aminoethoxy, 2'-O-amonioethyl (2'-OAE), 2'-O-methoxy, 2'-O-methyl, 2-guanidoethyl (2'-OGE), 2'-O, 4'-C-methylene (LNA), 2'-O-(methoxyethyl) (2'-OME) and 2'-O—(N-(methyl)acetamido) (2'-OMA).

Methods of gene therapy typically rely on the introduction into the cell of a nucleic acid molecule that alters the genotype of the cell. Introduction of the nucleic acid molecule can correct, replace, or otherwise alters the endogenous gene via genetic recombination. Methods can include introduction of an entire replacement copy of a defective gene, a heterologous gene, or a small nucleic acid molecule such as an oligonucleotide. This approach typically requires delivery systems to introduce the replacement gene into the cell, such as genetically engineered viral vectors.

Methods to construct expression vectors containing genetic sequences and appropriate transcriptional and translational control elements are well known in the art. These methods include in vitro recombinant DNA techniques, synthetic techniques, and in vivo genetic recombination. Expression vectors generally contain regulatory sequences necessary elements for the translation and/or transcription of the inserted coding sequence. For example, the coding sequence is preferably operably linked to a promoter and/or enhancer to help control the expression of the desired gene product. Promoters used in biotechnology are of different types according to the intended type of control of gene expression. They can be generally divided into constitutive promoters, tissue-specific or development-stage-specific promoters, inducible promoters, and synthetic promoters.

Viral vectors include adenovirus, adeno-associated virus, herpes virus, vaccinia virus, polio virus, AIDS virus, neuronal trophic virus, Sindbis and other RNA viruses, including these viruses with the HIV backbone. Also useful are any viral families which share the properties of these viruses which make them suitable for use as vectors. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promoter cassette is inserted into the viral genome in place of the removed viral DNA.

Gene targeting via target recombination, such as homologous recombination (HR), is another strategy for gene correction. Gene correction at a target locus can be mediated by donor DNA fragments homologous to the target gene (Hu, et al., Mol. Biotech., 29:197-210 (2005); Olsen, et al., J. Gene Med., 7:1534-1544 (2005)). One method of targeted recombination includes the use of triplex-forming oligonucleotides (TFOs) which bind as third strands to homopurine/homopyrimidine sites in duplex DNA in a sequence-specific manner. Triplex forming oigonucleotides can interact with either double-stranded or single-stranded nucleic acids. When triplex molecules interact with a target region, a structure called a triplex is formed, in which there are three strands of DNA forming a complex dependent on both Watson-Crick and Hoogsteen base-pairing. Triplex molecules are preferred because they can bind target regions with high affinity and specificity. It is preferred that the triplex forming molecules bind the target molecule with a Kd less than 10-6, 10-8, 10-10, or 10-12. Methods for targeted gene therapy using triplex-forming oligonucleotides (TFO's) and peptide nucleic acids (PNAs) are described in U.S. Published Application No. 20070219122 and their use for treating infectious diseases such as HIV are described in U.S. Published Application No. 2008050920. The triplex-forming molecules can also be tail clamp peptide nucleic acids (tcPNAs), such as those described in U.S. Published Application No. 2011/0262406.

Double duplex-forming molecules, such as a pair of pseudocomplementary oligonucleotides, can also induce recombination with a donor oligonucleotide at a chromosomal site. Use of pseudocomplementary oligonucleotides in targeted gene therapy is described in U.S. Published Application No. 2011/0262406.

2. Diagnostic Agents

Exemplary diagnostic materials include paramagnetic molecules, fluorescent compounds, magnetic molecules, and radionuclides. Suitable diagnostic agents include, but are not limited to, x-ray imaging agents and contrast media. Radionuclides also can be used as imaging agents. Examples of other suitable contrast agents include gases or gas emitting compounds, which are radioopaque. Liposomes can further include agents useful for determining the location of administered particles. Agents useful for this purpose include fluorescent tags, radionuclides and contrast agents.

3. CEST Agents

CEST agents are agents that can rapidly exchange protons with the surrounding water during an MRI. Examples of suitable CEST agents include, but are not limited to, L-arginine, barbituric acid, many analogs of barbituric acid with replacement of the hydrogen at the 5 position by an organic group, glycogen, glucose, myoinositol, glutamate, creatine and many polycationic peptides (e.g., poly-L-lysine). In some embodiments, the agent provides an offset from water of at least 2.0, 2.5, 3.0, 3.5, 4.0, 4.5, 5.0, or greater from water. In particular embodiments, the offset is about 5.0 ppm. In some embodiments, the agent is L-arginine, poly-L-lysine, or barbituric acid. In particular embodiments, the agent is barbituric acid.

III. Pharmaceutical Formulations

For those embodiments where the one or more therapeutic, prophylactic, and/or diagnostic agents are encapsulated within a liposomal nanoparticle and/or associated with the surface of the liposome, the percent drug loading is from about 1% to about 80%, from about 1% to about 50%, preferably from about 1% to about 40% by weight, more preferably from about 1% to about 20% by weight, most preferably from about 1% to about 10% by weight. The ranges above are inclusive of all values from 1% to 80%. For those embodiments where the agent is associated with the surface of the particle, the percent loading may be higher since the amount of drug is not limited by the methods of encapsulation. In some embodiments, the agent to be delivered may be encapsulated within a liposome and associated with the surface of the particle.

The formulations described herein contain an effective amount of liposomes ("MPPs") in a pharmaceutical carrier appropriate for administration to a mucosal surface, wherein the pharmaceutical carrier is adjusted to be hypotonic. One skilled in the art can routinely adjust tonicity of pharmaceutical carriers, once the desired tissue to be treated is identified, based on the preferred tonicity ranges described herein.

Tonicity is the 'effective osmolality' and is equal to the sum of the concentrations of the solutes which have the capacity to exert an osmotic force across the membrane. A number of different materials can be used to adjust tonicity. For example, the USP 29-NF 24 lists five excipients classified as "tonicity" agents, including dextrose, glycerin; potassium chloride; mannitol; and sodium chloride See, for example, United States Pharmacopeia Convention, Inc. *United States Pharmacopeia 29-National Formulary 24*. Rockville Md.: U.S. Pharmacopeia Convention, Inc.; 2005: 3261; Day, A. Dextrose. In: Rowe R C, Sheskey P J and Owen S C, eds. *Handbook of Pharmaceutical Excipients*. 5th ed. Washington D.C.: American Pharmaceutical Association; 2005: 231-233; Price J C. Glycerin. In: Rowe R C, Sheskey P J and Owen S C, eds. *Handbook of Pharmaceutical Excipients*. 5th ed. Washington D.C.: American Pharmaceutical Association; 2005: 301-303; Price J C. Glycerin. In: Rowe R C, Sheskey P J and Owen S C, eds. *Handbook of Pharmaceutical Excipients*. 5th ed. Washington D.C.: American Pharmaceutical Association; 2005: 301-303; Armstrong N A. Mannitol. In: Rowe R C, Sheskey P J and Owen S C, eds. *Handbook of Pharmaceutical Excipients*. 5th ed. Washington D.C.: American Pharmaceutical Association; 2005: 449-453; Owen S C. Sodium Chloride. In: Rowe R C, Sheskey P J and Owen S C, eds. *Handbook of Pharmaceutical Excipients*. 5th ed. Washington D.C.: American Pharmaceutical Association; 2005: 671-674. Mannitol is an example of a GRAS listed ingredient accepted for use as a food additive in Europe, included in the FDA Inactive Ingredients Database (IP, IM, IV, and SC injections; infusions; buccal, oral and sublingual tablets, powders and capsules; ophthalmic preparations; topical solutions), included in nonparenteral and parenteral medicines licensed in the UK and included in the Canadian Natural Health Products Ingredients Database. A 5.07% w/v aqueous solution is isoosmotic with serum.

Minimally hypotonic formulations, preferably ranging from 20-220 mOsm/kg, provide rapid and uniform delivery of MPP to the entire vaginal surface, with minimal risk of epithelial toxicity. There is a higher osmolality in the colon, such that vehicles with an osmolality above that of blood plasma (generally considered isotonic at ~300 mOsm/kg), leads to improvements in distribution in the colon. The range for improved colon distribution with a hypotonic vehicle in the colon is ~20 mOsm/kg-450 mOsm/kg.

A. Pulmonary Formulations

Pharmaceutical formulations and methods for the pulmonary administration of active agents to patients are known in the art.

The respiratory tract is the structure involved in the exchange of gases between the atmosphere and the blood stream. The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchioli which then lead to the ultimate respiratory zone, the alveoli, or deep lung, where the exchange of gases occurs.

Formulations can be divided into dry powder formulations and liquid formulations. Both dry powder and liquid formulations can be used to form aerosol formulations. The term aerosol as used herein refers to any preparation of a fine mist of particles, which can be in solution or a suspension, whether or not it is produced using a propellant.

1. Dry Powder Formulations

Dry powder formulations are finely divided solid formulations containing liposome carriers which are suitable for pulmonary administration. Dry powder formulations include, at a minimum, one or more liposome carriers which are suitable for pulmonary administration. Such dry powder formulations can be administered via pulmonary inhalation to a patient without the benefit of any carrier, other than air or a suitable propellant.

In other embodiments, the dry powder formulations contain one or more liposome gene carriers in combination with a pharmaceutically acceptable carrier. In these embodiments, the liposome gene carriers and pharmaceutical carrier can be formed into nano- or microparticles for delivery to the lung.

The pharmaceutical carrier may include a bulking agent or a lipid or surfactant. Natural surfactants such as dipalmitoylphosphatidylcholine (DPPC) are the most preferred. Synthetic and animal derived pulmonary surfactants include Exosurf—a mixture of DPPC with hexadecanol and tyloxapol added as spreading agents, Pumactant (Artificial Lung Expanding Compound or ALEC)—a mixture of DPPC and PG, KL-4-composed of DPPC, palmitoyl-oleoyl phosphatidylglycerol, and palmitic acid, combined with a 21 amino acid synthetic peptide that mimics the structural characteristics of SP-B, Venticute—DPPC, PG, palmitic acid and recombinant SP-C, Alveofact—extracted from cow lung lavage fluid, Curosurf—extracted from material derived from minced pig lung, Infasurf—extracted from calf lung lavage fluid, and Survanta—extracted from minced cow lung with additional DPPC, palmitic acid and tripalmitin. Exosurf, Curosurf, Infasurf, and Survanta are the surfactants currently FDA approved for use in the U.S.

The pharmaceutical carrier may also include one or more stabilizing agents or dispersing agents. The pharmaceutical carrier may also include one or more pH adjusters or buffers. Suitable buffers include organic salts prepared from organic acids and bases, such as sodium citrate or sodium ascorbate. The pharmaceutical carrier may also include one or more salts, such as sodium chloride or potassium chloride.

Dry powder formulations are typically prepared by blending one or more liposome carriers with one or more pharmaceutically acceptable carriers. Optionally, additional active agents may be incorporated into the mixture as discussed below. The mixture is then formed into particles suitable for pulmonary administration using techniques known in the art, such as lyophilization, spray drying, agglomeration, spray coating, coacervation, low temperature casting, milling (e.g., air-attrition milling (jet milling), ball milling), high pressure homogenization, and/or super-critical fluid crystallization.

An appropriate method of particle formation can be selected based on the desired particle size, particle size distribution, and particle morphology desired for the formulation. In some cases, the method of particle formation is selected so as to produce a population of particles with the desired particle size, particle size distribution for pulmonary administration. Alternatively, the method of particle formation can produce a population of particles from which a population of particles with the desired particle size, particle size distribution for pulmonary administration is isolated, for example by sieving.

It is known in the art that particle morphology affects the depth of penetration of a particle into the lung. Accordingly, dry powder formulations is processed into particles having the appropriate mass median aerodynamic diameter (MMAD), tap density, and surface roughness to achieve delivery of the one or more active agents to the desired region(s) of the lung. For example, preferred particle morphologies for delivery to the deep lung are known in the art, and are described, for example, in U.S. Pat. No. 7,052,678 to Vanbever, et al.

Particles having a mass median aerodynamic diameter (MMAD) of greater than about 5 microns generally do not reach the lung; instead, they tend to impact the back of the throat and are swallowed. Particles having diameters of about 3 to about 5 microns are small enough to reach the upper- to mid-pulmonary region (conducting airways), but may be too large to reach the alveoli. Smaller particles, (i.e., about 0.5 to about 3 microns), are capable of efficiently reaching the alveolar region. Particles having diameters smaller than about 0.5 microns can also be deposited in the alveolar region by sedimentation.

The precise particle size range effective to achieve delivery to the alveolar region will depend on several factors, including the tap density of particles being delivered. Generally speaking, as tap density decreases, the MMAD of particles capable of efficiently reaching the alveolar region of the lungs increases. Therefore, in cases of particles with low tap densities, particles having diameters of about 3 to about 5 microns, about 5 to about 7 microns, or about 7 to about 9.5 microns can be efficiently delivered to the lungs. The preferred aerodynamic diameter for maximum deposition within the lungs can be calculated. See, for example, U.S. Pat. No. 7,052,678 to Vanbever, et al.

Microparticles cannot diffuse through mucus even if their surface is muco-resistant. However, mucus-penetrating particles can be encapsulated in microparticles to impact upper lung, and subsequently release the liposomes. In some cases, the particles are spherical or ovoid in shape. The particles can have a smooth or rough surface texture. The particles may also be coated with a polymer or other suitable material to control release of one or more active agents in the lungs.

Dry powder formulations can be administered as dry powder using suitable methods known in the art. Alternatively, the dry powder formulations can be suspended in the liquid formulations described below, and administered to the lung using methods known in the art for the delivery of liquid formulations.

2. Liquid Formulations

Liquid formulations contain one or more liposome carriers suspended in a liquid pharmaceutical carrier. Suitable liquid carriers include, but are not limited to water, saline, and other physiologically acceptable aqueous solutions containing salts and/or buffers, such as phosphate buffered saline (PBS), Ringer's solution, and isotonic sodium chloride, or any other aqueous solution acceptable for administration to an animal or human, which is adjusted to the desired hypotonicity.

Preferably, liquid formulations are isotonic relative to physiological fluids and of approximately the same pH, ranging e.g., from about pH 4.0 to about pH 7.4, more preferably from about pH 6.0 to pH 7.0. The liquid pharmaceutical carrier can include one or more physiologically compatible buffers, such as a phosphate buffers. One skilled in the art can readily determine a suitable saline content and pH for an aqueous solution for pulmonary administration.

Liquid formulations may include one or more suspending agents, such as cellulose derivatives, sodium alginate, polyvinylpyrrolidone, gum tragacanth, or lecithin. Liquid formulations may also include one or more preservatives, such as ethyl or n-propyl p-hydroxybenzoate.

In some cases the liquid formulation may contain one or more solvents that are low toxicity organic (i.e. nonaqueous) class 3 residual solvents, such as ethanol, acetone, ethyl acetate, tetrahydofuran, ethyl ether, and propanol. These solvents can be selected based on their ability to readily aerosolize the formulation. Any such solvent included in the liquid formulation should not detrimentally react with the one or more active agents present in the liquid formulation. The solvent should be sufficiently volatile to enable formation of an aerosol of the solution or suspension. Additional solvents or aerosolizing agents, such as a freon, alcohol, glycol, polyglycol, or fatty acid, can also be included in the liquid formulation as desired to increase the volatility and/or alter the aerosolizing behavior of the solution or suspension.

Liquid formulations may also contain minor amounts of polymers, surfactants, or other excipients well known to those of the art. In this context, "minor amounts" means no excipients are present that might adversely affect uptake of the one or more active agents in the lungs.

3. Aerosol Formulations

The dry powder and liquid formulations described above can be used to form aerosol formulations for pulmonary administration. Aerosols for the delivery of therapeutic agents to the respiratory tract are known in the art. The term aerosol as used herein refers to any preparation of a fine mist of solid or liquid particles suspended in a gas. In some cases, the gas may be a propellant; however, this is not required. Aerosols may be produced using a number of standard techniques, including as ultrasonication or high pressure treatment.

In some cases, a device is used to administer the formulations to the lungs. Suitable devices include, but are not limited to, dry powder inhalers, pressurized metered dose inhalers, nebulizers, and electrohydrodynamic aerosol devices. Inhalation can occur through the nose and/or the mouth of the patient. Administration can occur by self-administration of the formulation while inhaling or by administration of the formulation via a respirator to a patient on a respirator.

B. Topical and Ophthalmic Formulations

Topical or enteral formulations can be prepared as aqueous compositions using techniques is known in the art. Typically, such compositions can be prepared as solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, emulsomes, sprays, gels, creams or ointments.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include agents, for example, sugars or sodium chloride, to adjust the tonicity.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-alanine, sodium N-lauryl-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for administration upon reconstitution. Suitable buffers include, but are not limited to, phosphate buffers, acetate buffers, and citrate buffers.

Water soluble polymers are often used in pharmaceutical formulations. Suitable water-soluble polymers include, but are not limited to, polyvinylpyrrolidone, dextran, carboxymethylcellulose, and polyethylene glycol.

Sterile solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

Pharmaceutical formulations for ocular administration are preferably in the form of a sterile aqueous solution or suspension of particles formed from one or more polymer-drug conjugates. Acceptable solvents include, for example, water, Ringer's solution, phosphate buffered saline (PBS), and isotonic sodium chloride solution, which are then adjusted to the desired hypotonicity. The formulation may also be a sterile solution, suspension, or emulsion in a nontoxic, parenterally acceptable diluent or solvent such as 1,3-butanediol.

In some instances, the formulation is distributed or packaged in a liquid or semi-solid form such as a solution (eye drops), suspension, gel, cream or ointment. Alternatively, formulations for ocular administration can be packed as a solid, obtained, for example by lyophilization of a suitable liquid formulation. The solid can be reconstituted with an appropriate carrier or diluent prior to administration.

Solutions, suspensions, or emulsions for ocular administration may be buffered with an effective amount of buffer necessary to maintain a pH suitable for ocular administration. Suitable buffers are well known by those skilled in the art and some examples of useful buffers are acetate, borate, carbonate, citrate, and phosphate buffers. Solutions, suspensions, or emulsions for ocular administration may also contain one or more tonicity agents to adjust the isotonic range of the formulation. Suitable tonicity agents are well known in the art and some examples include glycerin, mannitol, sorbitol, sodium chloride, and other electrolytes.

Solutions, suspensions, or emulsions for ocular administration may also contain one or more preservatives to prevent bacterial contamination of the ophthalmic preparations. Suitable preservatives are known in the art, and include polyhexamethylenebiguanidine (PHMB), benzalkonium chloride (BAK), stabilized oxychloro complexes (otherwise known as Purite®), phenylmercuric acetate, chlorobutanol, sorbic acid, chlorhexidine, benzyl alcohol, parabens, thimerosal, and mixtures thereof.

Solutions, suspensions, or emulsions for ocular administration may also contain one or more excipients known in the art, such as dispersing agents, wetting agents, and suspending agents.

In still other embodiments, the liposomes are formulated for topical administration to mucosa. Suitable dosage forms for topical administration include creams, ointments, salves, sprays, gels, lotions, and emulsions. The compositions may contain one or more chemical penetration enhancers, membrane permeability agents, membrane transport agents, emollients, surfactants, stabilizers, and combination thereof.

In some embodiments, the liposomes can be administered as a liquid formulation, such as a solution or suspension, a semi-solid formulation, such as a gel, a lotion or an ointment, or a solid formulation. A "gel" is a colloid in which the dispersed phase has combined with the continuous phase to produce a semisolid material, such as jelly.

In some embodiments, the liposomes are formulated as liquids, including solutions and suspensions, such as eye drops or as a semi-solid formulation, such as ointment or lotion for topical application to mucosa, such as the eye or vaginally or rectally.

The formulation may contain one or more excipients, such as emollients, surfactants, and emulsifiers.

"Emollients" are an externally applied agent that softens or soothes skin and are generally known in the art and listed in compendia, such as the "Handbook of Pharmaceutical Excipients", 4$^{th}$ Ed., Pharmaceutical Press, 2003. These include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In one embodiment, the emollients are ethylhexylstearate and ethylhexyl palmitate.

"Surfactants" are surface-active agents that lower surface tension and thereby increase the emulsifying, foaming, dispersing, spreading and wetting properties of a product. Suitable non-ionic surfactants include emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In one embodiment, the non-ionic surfactant is stearyl alcohol.

"Emulsifiers" are surface active substances which promote the suspension of one liquid in another and promote the formation of a stable mixture, or emulsion, of oil and water. Common emulsifiers are: metallic soaps, certain animal and vegetable oils, and various polar compounds. Suitable emulsifiers include acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxypropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In one embodiment, the emulsifier is glycerol stearate.

Suitable classes of penetration enhancers are known in the art and include, but are not limited to, fatty alcohols, fatty acid esters, fatty acids, fatty alcohol ethers, amino acids, phospholipids, lecithins, cholate salts, enzymes, amines and amides, complexing agents (liposomes, cyclodextrins, modified celluloses, and diimides), macrocyclics, such as macrocylic lactones, ketones, and anhydrides and cyclic ureas, surfactants, N-methyl pyrrolidones and derivatives thereof, DMSO and related compounds, ionic compounds, azone and related compounds, and solvents, such as alcohols, ketones, amides, polyols (e.g., glycols). Examples of these classes are known in the art.

An "oil" is a composition containing at least 95% wt of a lipophilic substance. Examples of lipophilic substances include but are not limited to naturally occurring and synthetic oils, fats, fatty acids, lecithins, triglycerides and combinations thereof.

A "continuous phase" refers to the liquid in which solids are suspended or droplets of another liquid are dispersed, and is sometimes called the external phase. This also refers to the fluid phase of a colloid within which solid or fluid particles are distributed. If the continuous phase is water (or another hydrophilic solvent), water-soluble or hydrophilic drugs will dissolve in the continuous phase (as opposed to being dispersed). In a multiphase formulation (e.g., an emulsion), the discreet phase is suspended or dispersed in the continuous phase.

An "emulsion" is a composition containing a mixture of non-miscible components homogenously blended together. In particular embodiments, the non-miscible components include a lipophilic component and an aqueous component. An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. The oil phase may consist at least in part of a propellant, such as an HFA propellant. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

A sub-set of emulsions are the self-emulsifying systems. These drug delivery systems are typically capsules (hard shell or soft shell) comprised of the drug dispersed or dissolved in a mixture of surfactant(s) and lipophilic liquids such as oils or other water immiscible liquids. When the capsule is exposed to an aqueous environment and the outer gelatin shell dissolves, contact between the aqueous medium and the capsule contents instantly generates very small emulsion droplets. These typically are in the size range of micelles or liposomes. No mixing force is required to generate the emulsion as is typically the case in emulsion formulation processes.

A "lotion" is a low- to medium-viscosity liquid formulation. A lotion can contain finely powdered substances that are in soluble in the dispersion medium through the use of suspending agents and dispersing agents. Alternatively, lotions can have as the dispersed phase liquid substances that are immiscible with the vehicle and are usually dispersed by means of emulsifying agents or other suitable stabilizers. In one embodiment, the lotion is in the form of an emulsion having a viscosity of between 100 and 1000 centistokes. The fluidity of lotions permits rapid and uniform application over a wide surface area. Lotions are typically intended to dry on the skin leaving a thin coat of their medicinal components on the skin's surface.

A "cream" is a viscous liquid or semi-solid emulsion of either the "oil-in-water" or "water-in-oil type". Creams may contain emulsifying agents and/or other stabilizing agents. In one embodiment, the formulation is in the form of a cream having a viscosity of greater than 1000 centistokes, typically in the range of 20,000-50,000 centistokes. Creams are often time preferred over ointments as they are generally easier to spread and easier to remove.

The difference between a cream and a lotion is the viscosity, which is dependent on the amount/use of various oils and the percentage of water used to prepare the formulations. Creams are typically thicker than lotions, may have various uses and often one uses more varied oils/butters, depending upon the desired effect upon the skin. In a cream formulation, the water-base percentage is about 60-75% and the oil-base is about 20-30% of the total, with the other percentages being the emulsifier agent, preservatives and additives for a total of 100%.

An "ointment" is a semisolid preparation containing an ointment base and optionally one or more active agents. Examples of suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy that ointments prepared with the same components.

A "gel" is a semisolid system containing dispersions of small or large molecules in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Suitable gelling agents include, but are not limited to, modified celluloses, such as hydroxypropyl cellulose and hydroxyethyl cellulose; Carbopol homopolymers and copolymers; and combinations thereof. Suitable solvents in the liquid vehicle include, but are not limited to, diglycol monoethyl ether; alklene glycols, such as propylene glycol; dimethyl isosorbide; alcohols, such as isopropyl alcohol and ethanol. The solvents are typically selected for their ability to dissolve the drug. Other additives, which improve the skin feel and/or emolliency of the formulation, may also be incorporated. Examples of such additives include, but are not limited, isopropyl myristate, ethyl acetate, $C_{12}$-$C_{15}$ alkyl benzoates, mineral oil, squalane, cyclomethicone, capric/caprylic triglycerides, and combinations thereof.

Foams consist of an emulsion in combination with a gaseous propellant or gas-emitting component.

Buffers are used to control pH of a composition. Preferably, the buffers buffer the composition from a pH of about 4 to a pH of about 7.5, more preferably from a pH of about 4 to a pH of about 7, and most preferably from a pH of about 5 to a pH of about 7.

D. Enteral Formulations

Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art. Formulations may be prepared using one or more pharmaceutically acceptable excipients, including diluents, preservatives, binders, lubricants, disintegrators, swelling agents, fillers, stabilizers, and combinations thereof.

Excipients, including plasticizers, pigments, colorants, stabilizing agents, and glidants, may also be used to form coated compositions for enteral administration. Delayed release dosage formulations may be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.:

Williams and Wilkins, 1995). These references provide information on excipients, materials, equipment and process for preparing tablets and capsules and delayed release dosage forms of tablets, capsules, and granules.

The liposomes may be coated, for example to delay release once the particles have passed through the acidic environment of the stomach. Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

Stabilizers are used to inhibit or retard drug decomposition reactions that include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

IV. Methods of Making Mucus-Penetrating Liposomal Particles

The liposomes described herein can be prepared by a variety of techniques known in the art. The method selected is dependent on a variety of factors, such as: (1) the physicochemical characteristics of the material to be entrapped and those of the liposomal ingredients; (2) the nature of the medium in which the lipid vesicles are dispersed; (3) the effective concentration of the entrapped substance and its potential toxicity; (4) additional processes involved during application/delivery of the vesicles; (5) optimum size, polydispersity and shelf-life of the vesicles for the intended application; and (6) batch-to-batch reproducibility and possibility of large-scale production of safe and efficient liposomal products.

Formation of liposomes and nanoliposomes is not a spontaneous process. Lipid vesicles are formed when phospholipids such as lecithin are placed in water and consequently form one bilayer or a series of bilayers, each separated by water molecules, once enough energy is supplied. Liposomes can be created by sonicating phosphatidylcholine rich phospholipids in water. Low shear rates create multilamellar liposomes, which have many layers like an onion.

Continued high-shear sonication tends to form smaller unilamellar liposomes. In this technique, the liposome contents are the same as the contents of the aqueous phase. Sonication is generally considered a "gross" method of preparation as it can damage the structure of the drug to be encapsulated. Newer methods such as extrusion and Mozafari method are employed to produce materials for animal (e.g., human) use.

In some embodiments, liposomal particles are prepared using a conventional thin film hydration and extrusion method. The lipid, PEG-conjugated lipid, and stabilizer, if present, are dissolved in an organic solvent (e.g., chloroform) at pre-determined molar ratios. A small proportion of a labeled-lipid, such as rhodamine labeled PE (Rho-PE), can be added to the mixture to enable visualization of the liposomal particles via fluorescence microscopy. The mixture is placed in a rotavap with reduced atmosphere pressure to evaporate the organic solvent. The resulting lipid film is hydrated, such as with phosphate buffered saline (PBS), while agitated using a water bath sonicator to form multilamellar vehicles (MLV). The suspension is subsequently extruded through polycarbonate filters with pore sizes of 400 nm and 200 nm to generate unilamellar vehicles (LUV, i.e., liposomes with single bilayer membrane).

IV. Methods of Using Mucus-Penetrating Liposomal Particles

The mucus-penetrating liposomal nanoparticles described herein can be used to deliver a variety of therapeutic, prophylactic, and/or diagnostic agents. In some embodiments, the agent or agents are hydrophilic or water-soluble, such as hydrophilic small molecule drugs, monoclonal antibodies and other protein-derived products. These agents are difficult to load into polymeric nanoparticles due to the hydrophobic nature of the particle core. This hydrophobic core is necessary in order to facilitate particle formation. In contrast, the lipid-based MPP described herein can be readily loaded with hydrophilic and hydrophobic substances. When particles are formulated, lipids self-assemble into bilayer membranes, forming a lipophilic shell for hydrophobic payloads, and entrapping an aqueous solution with hydrophilic payloads in the center.

The drug-loaded lipid-based particles described herein are able to diffuse rapidly and remain integral in human cervicovaginal mucus (CVM). The lipid-based MPP are expected to cross the mucus barrier timely to avoid aggregation or removal by mucus, and thus can distribute more uniformly, stay longer and provide more effective treatment for diseases on mucosal tissues, such as cervical cancers and sexually transmitted diseases (STD) as well as diseases of the colon, nose, lungs, and eyes.

The particles described here can also be used to provide an improved method for evaluating temporal retention and spatial distribution of the particles in the animal. Previous methods to evaluate the temporal retention and spatial distribution of nanocarriers dosed in animals mostly required labeling the carriers fluorescently and dissecting the animals for observation and quantification. In contrast, by encapsulating a CEST MRI contrast agent, in the lipid-based MPP, the carriers were monitored using CEST MRI tools in live animals over time.

A. Chemical Exchange Saturation Transfer (CEST)

Chemical exchange saturation transfer (CEST) is a magnetic resonance imaging (MRI) contrast enhancement technique that enables indirect detection of contrast agents with exchangeable protons. Contrast agents with exchangeable protons including, but not limited to, L-arginine, barbituric acid, many analogs of barbituric acid with replacement of the hydrogen at the 5 position by an organic group, glycogen, glucose, myoinositol, glutamate, creatine and many polycationic peptides have been identified as potential in vivo CEST agents. Exogenous agents, such as diagnostic agents or contrast agents, can also be used for in vivo imaging. CEST technology has a number of indispensable features, such as the possibility of simultaneous detection of multiple 'colors' of agents and of changes in their environment (e.g. pH, metabolites, etc.) through MR contrast.

CEST exploits the ability of Nuclear Magnetic Resonance (NMR) to resolve different signals arising from protons on different molecules. By selectively saturating a particular proton signal (associated with a particular molecule or CEST agent) that is in exchange with surrounding water molecules, the MRI signal from the surrounding bulk water molecules is also attenuated. Images obtained with and without the RF saturating pulse reveal the location of the CEST agent. The chemical exchange must be in the intermediate regime where exchange is fast enough to efficiently saturate the bulk water signal but slow enough that there is a chemical shift difference between the exchangeable proton and the water proton resonances. The magnitude of the CEST effect therefore depends on both the exchange rate and the number of exchangeable protons.

CEST has three main advantages over traditional molecular imaging techniques: (1) the image contrast is controlled with radio-frequency (RF) pulses and can be turned on/off at will; (2) The molecules of interest, in some cases, can be directly detected, eliminating the need for contrast agent to be delivered to, and to specifically react with, the molecule of interest; (3) A variant of the CEST technique, known as PARACEST, may be much more sensitive than traditional molecular imaging techniques and should be able to detect nanomolar concentrations. PARACEST typically relies on water exchange between the bulk water and water bound to paramagnetic Lanthanide complexes. Saturation of the Lanthanide ion bound water resonance leads to attenuation of the bulk water signal via water exchange. The large paramagnetic chemical shift of the bound water molecules allows them to tolerate much faster exchange rates with the bulk water while still while still remaining in the intermediate exchange regime, thereby providing much more efficient saturation of the bulk water signal and much greater CEST sensitivity.

CEST can be used to monitor drug delivery at a desired site from the mucus-penetrating liposomal particles described herein. For example, CEST can be used to monitor the vaginal drug delivery of liposomes for local treatment of cervical tumors by coencapsulating diamagnetic CEST contrast agents and drugs within the liposomal particles described herein. In vitro and in vivo images with PEG-coated liposomes show frequency offsets further from water (at 5 ppm) than previous designs. The integration of CEST and pegylated liposomal nanoparticles provides a non-invasive and quantitative way to evaluate the performance of these particles in vivo in preclinical studies.

EXAMPLES

Example 1. Preparation of Mucus-Penetrating Liposomal Particles

Liposomal particles were prepared using a conventional thin film hydration and extrusion method. 12 mg of a mixture of phosphatidylcholine (PC, e.g., egg PC or hydrogenated soy PC), PEG-phosphatidylethanolamine (PEG-PE) and cholesterol (CHOL) were dissolved in chloroform at pre-determined molar ratios. A small proportion of Rhodamine labeled PE (Rho-PE) was added to the mixture to enable visualization of the liposomal particles via fluorescence microscopy. The mixture was placed in a rotavap with reduced atmosphere pressure to evaporate the organic solvent. The resulting lipid film was hydrated with phosphate buffered saline (PBS) while agitated using a water bath sonicator to form multi-lamellar vehicles (MLV). The suspension was subsequently extruded through polycarbonate filters with pore sizes of 400 nm and 200 nm to generate unilamellar vehicles (LUV, i.e., liposomes with single bilayer membrane).

To load CEST agent (barbituric acid (BA)), the lipid thin film was hydrated with PBS buffer containing 25 mg/mL BA before annealing and agitation via sonication. To load drug (doxorubicin (DOX)), the MLV suspension was mixed with PBS buffer containing 2 mg/mL DOX before sonication and extrusion.

Though the thin film hydration and extrusion method was employed, liposomal particles can be prepared using other methods known in the art and should exhibit similar properties as long as the composition of the liposomal particles does not change.

A scheme of the composition of liposomal particles is shown in FIG. 1.

Example 2. Characterization of Liposomal Particles

The size and zeta-potential of liposomal particles were measured using dynamic light scattering and laser Doppler electrophoresis, respectively. Data are shown in Table 2.

TABLE 2

Compositions of liposomal particles and their basic characterization

| Molar Ratio (%) (PC:CHOL:Rho-PE:PEG-PE) | Sample Abbreviation | Size (Z-ave) (d. nm) | Polydispersity Index | Zeta Potential (mV) |
|---|---|---|---|---|
| 0.28:0.72:0.002:0.00 | 0% PEG | 222 | 0.41 | −2.5 |
| 0.26:0.68:0.002:0.05 | 5% PEG | 160 | 0.16 | −2.0 |

TABLE 2-continued

Compositions of liposomal particles and their basic characterization

| Molar Ratio (%) (PC:CHOL:Rho-PE:PEG-PE) | Sample Abbreviation | Size (Z-ave) (d. nm) | Polydispersity Index | Zeta Potential (mV) |
|---|---|---|---|---|
| 0.25:0.65:0.002:0.10 | 10% PEG | 175 | 0.06 | −2.2 |
| 0.22:0.58:0.002:0.20 | 20% PEG | 132 | 0.15 | −1.6 |

The size of the liposomal particles of all tested compositions ranged from 130 to 230 nm, well below the mesh dimension of human CVM (estimated to be >500 nm). Higher ratio of PEG-conjugated lipids reduced the size of the particles, likely due to the formation of liposomal micelles. A high proportion of cholesterol was used to enhance the stability of the liposomal particles.

Example 3. Stability of Mucus-Penetrating Liposomal Particles

Figure 2A:
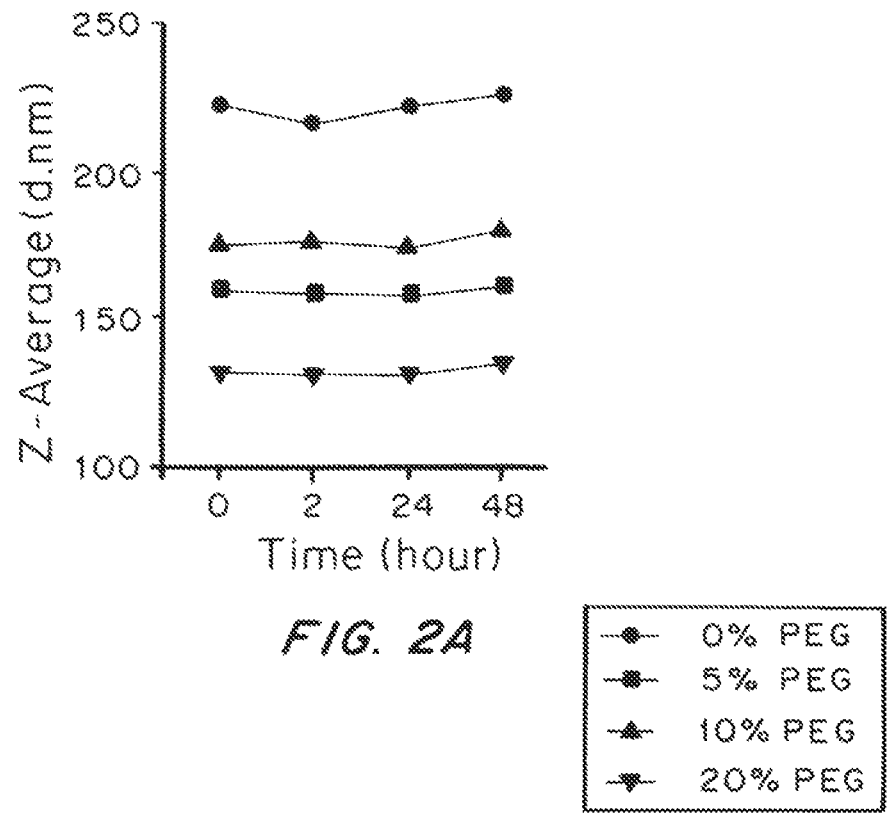
FIG. 2A is a graph showing the diameter of the liposomal nanoparticles as a function of time (hours) for liposomal nanoparticles containing different amounts of polyethylene glycol (PEG).
Figure 2B:
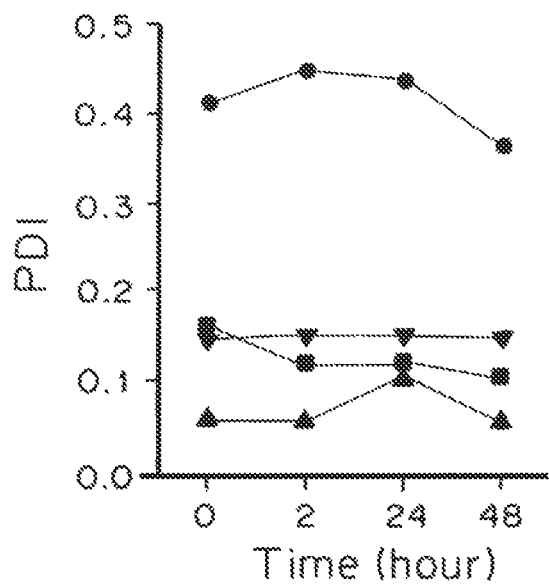
FIG. 2B is a graph showing the polydispersity of the liposomal nanoparticles as a function of time (hours) for liposomal nanoparticles containing different amounts of PEG.

To test the stability of the liposomal particles of different compositions, we incubated the particles in phosphate buffered saline (PBS) at 37° C. and monitored the change of size and polydispersity over time, as shown in FIG. 2. The size and polydispersity index (PDI) of the particles were steady for all the experimental groups for over 48 hrs. However, the PDI of liposomal particles with no PEG was consistently higher than other experimental group, indicating their poorer quality and weaker stability as compared to the PEGylated ones.

Example 4. Diffusivity and Stability of Liposomal Particles in Mucus

The diffusivity of the liposomal particles with different compositions in human CVM samples was evaluated. 0.6 µl of diluted liposomal particles were added to 20 µl freshly collected, undiluted human CVM. Samples were stored at room temperature and at different time points, 20 sec movies were acquired to record the trajectory of the particles. The qualitative observation of the mobility and the stability of the liposomal particles are summarized in Table 3.

TABLE 3

Compositions of liposomal particles and their basic characterization

| | Proportion of moving particles (Qualitative Observation) | | |
|---|---|---|---|
| Sample | 2 hr* | 15 hr* | Stability |
| 0% PEG | 0% | 0% | Heavy aggregation |
| 5% PEG | 20% | 10% | Aggregation |
| 10% PEG | 80% | ~30-70% | Some aggregation |
| 20% PEG | ~100% | ~90-100% | Well dispersed |

*Time post sample preparation.

Liposomal particles without any PEG coating were strongly immobilized and heavily aggregated by mucus. Incorporating PEG-PE facilitated the diffusion as well as the stability of the particles in mucus. The higher the proportion of PEG-PE, the more liposomal particles were freely diffusive, and more uniformly dispersed in mucus. Specifically, liposomal particles with 10% or 20% PEG remained mostly mobile and intact in mucus for at least 15 hr, long enough for particles to penetrate the mucus layers and reach the underlying epithelium. "Mobile" was defined as those particles which traveled a distance of over 10 times its radius (about 100 nm) in a 20 second movie, which corresponds to 0.1 $\mu m^2$/sec.

Typically, PEGylated liposomal particles (e.g., stealth liposomes for intravenous injection) are composed of ~3 to 7 mol % PEG-conjugated lipid molecules. However, to enable particles to penetrate human mucus, it was found that a higher proportion of PEG (i.e., 10-20 mol %) is necessary.

Example 5. Evaluation of Mucus-Penetrating Liposomal Particles for Chemical Exchange Saturation Transfer (CEST)

Animal Preparation

C57BL/6 mice were given Depo-Provera (3 mg/mouse) by subcutaneous injection on the right flank 4 days prior to tumor inoculation. Luciferase expressing C3.34 cells were then implanted into the intravaginal cavity of mice, and bioluminescence imaging was used to monitor the growth of the tumor.

CEST Imaging

Mice were anesthetized using isoflurane and positioned in a 11.7 T horizontal bore Bruker Biospec scanner, and were imaged before and after intravaginal administration of 20 ul of BA/DOX PEGylated liposomes.

CEST images were acquired through collection of two sets of saturation images, a water saturation shift referencing (WASSR)6 set for B0 mapping and a CEST data set for characterizing contrast. For the CEST images: tsat=3 sec, B1=4.7 uT, TR=5 sec, with offset incremented from −6 to +6 ppm (0.3 ppm steps) with a fat suppression pulse. The acquisition parameters were: TR=5.0 sec, effective TE=21.6 ms, RARE factor=8. The CEST images were acquired every 30 min after the liposome administration up to 2 hrs.

Data Analysis

MR images were processed using custom-written Matlab scripts with the CEST contrast was the magnetization transfer ratio (for NH pMTRasym %=(S-$\Delta\omega$-S$\Delta\omega$)/S0×100%) protons at $\Delta\omega$=5 ppm.

Figure 3:
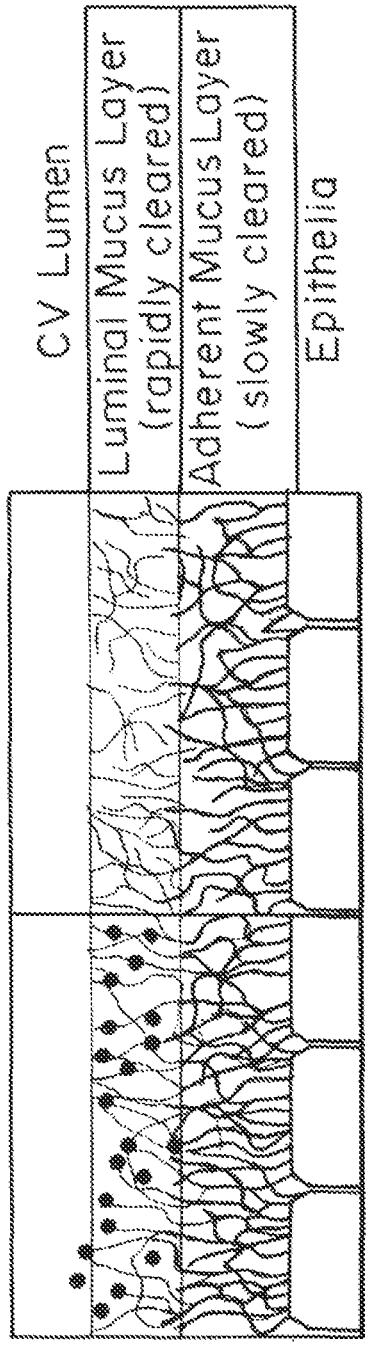
FIG. 3 is a schematic showing the penetration of mucus-penetrating particles compared to non-mucus-penetrating particles.
Figure 3:
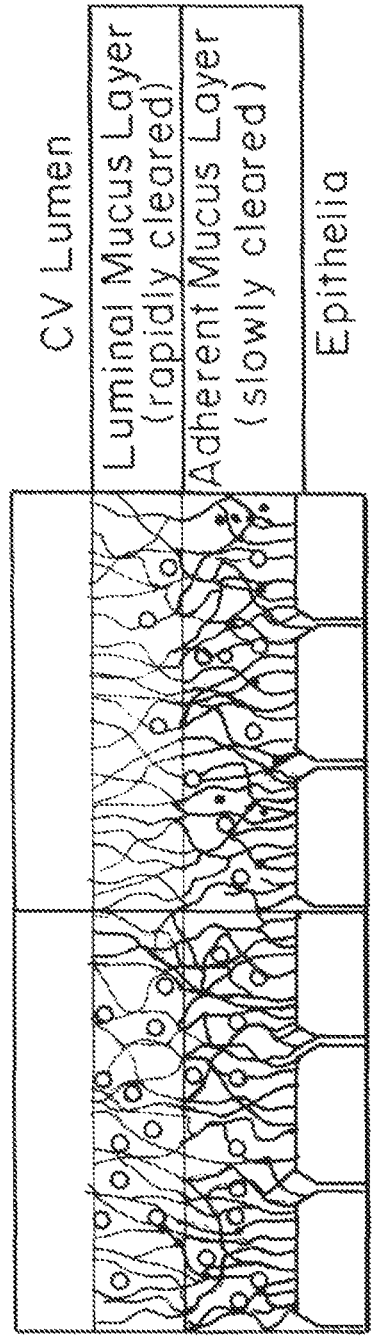

FIG. 3 is a representation of the rationale for designing liposomal nanoparticles for imaging particle-based therapy of cervical tumors.

Figure 4:
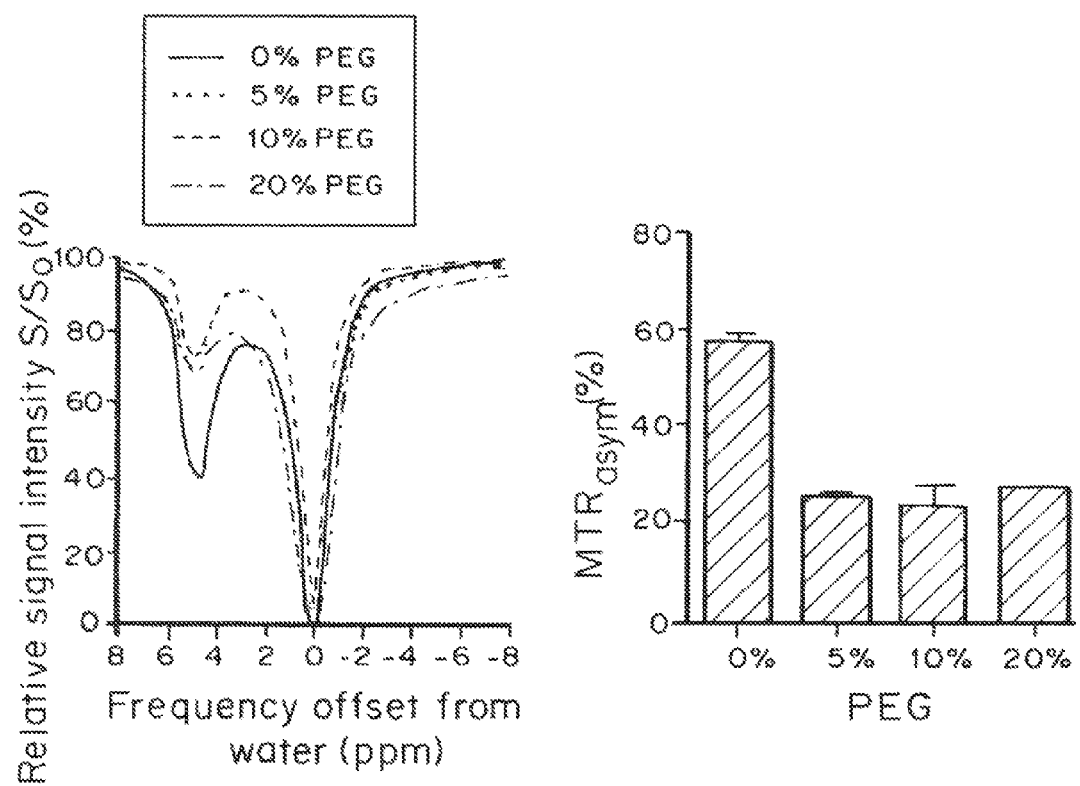
FIG. 4 shows the relative signal intensity as a function of frequency offset from water for liposomal nanoparticles prepared with different amounts of PEG-conjugated lipid.

The results of the in vitro CEST imaging for various liposomal particles are shown in FIG. 4. The in vitro CEST contrast for these liposomes coated with 0%, 5%, 10% and 20% PEG was 53%, 27%, 25% and 23% respectively at 5 ppm. These particles were stable over 2 days in vitro with no significant change in the size and PDI as described above.

FIG. 4A shows the optimization of CEST contrast for liposomal particles containing 30, 50, and 70 mol percent cholesterol. Liposomes with >10% PEG and 50 mol % of cholesterol were stable and have high CEST contrast. The CEST liposomes could be visualized using MRI after local administration and their distribution could be traced over 2 hrs. The liposomes were located close to the opening of the vaginal cavity (ROI1), and seemed to stay in a distal region (ROI2) inside the vagina. The contrast in ROI1 and ROI2 increased right after administration and over the first 60 min. Interestingly, the contrast in ROI2 was much higher than that in ROI1 at 90 min post-administration, and it is higher than that of pre-administration. This indicated that liposomes could be retained inside the vagina for at least 2 hrs.

We claim:

1. Mucus penetrating liposomal nanoparticles having an average diameter between 130 nm and 300 nm, comprising one or more poly(ethylene glycol) (PEG)-conjugated lipids, one or more lipids, a stabilizer, and one or more therapeutic, prophylactic, and/or diagnostic agents,
wherein the concentration of the one or more PEG-conjugated lipids is between about 8 mole percent and about 30 mole percent of the total of the PEG-conjugated lipids, the lipids, and the stabilizer, and
wherein the concentration of the stabilizer is from about 5 mole percent to about 65 mole percent of the total of the PEG-conjugated lipids, the lipids, and the stabilizer,
wherein at least 50% of the liposomal nanoparticles are mobile in freshly collected, undiluted human cervicovaginal mucus (CVM) at 2 hours and at least 30% of the liposomal nanoparticles are mobile in freshly collected, undiluted human CVM at 15 hours.

2. The liposomal nanoparticles of claim 1, wherein the concentration of the one or more PEG-conjugated lipids is from about 10 mole percent to about 20 mole percent of the total of the PEG-conjugated lipids, the lipids, and the stabilizer.

3. The liposomal nanoparticles of claim 1, wherein the one or more PEG-conjugated lipids is a PEG-conjugated phospholipid.

4. The liposomal nanoparticles of claim 3, wherein the PEG-conjugated phospholipid is selected from the group consisting of phosphatidic acid, phosphatidylethanolamine, phosphatidylcholine, phosphatidylserine, phosphoinositides, ceramide phosphorylcholine, and ceramide phosphorylethanolamine.

5. The liposomal nanoparticles of claim 4, wherein the PEG-conjugated phospholipid is PEG-phosphatidylethanolamine (PEG-PE).

6. The liposomal nanoparticles of claim 1, wherein the one or more lipids are selected from the group consisting of fatty acids, glycerolipids, glycerophospholipids, sphingolipids, saccharolipids, polyketides; sterol lipids and prenol lipids.

7. The liposomal nanoparticles of claim 6, wherein the one or more lipids is a phospholipid.

8. The liposomal nanoparticles of claim 7, wherein the phospholipid is phosphatidylcholine (PC).

9. The liposomal nanoparticles of claim 1, wherein the stabilizer is cholesterol.

10. The liposomal nanoparticles of claim 1, wherein the concentration of the stabilizer is from about 10 mole percent to about 40 mole percent of the total of the PEG-conjugated lipids, the lipids, and the stabilizer.

11. The liposomal nanoparticles of claim 1, wherein the liposomal nanoparticles further comprise a therapeutic agent, prophylactic agent, diagnostic agent, or combinations thereof.

12. The liposomal nanoparticles of claim 11, wherein the agent is a therapeutic agent.

13. The liposomal nanoparticles of claim 12, wherein the therapeutic agent is an antitumor agent.

14. The liposomal nanoparticles of claim 13, wherein the antitumor agent is doxorubicin.

15. The liposomal nanoparticles of claim 1, further comprising a chemical exchange saturation transfer (CEST) agent.

16. The liposomal nanoparticles of claim 15, wherein the CEST agent is barbituric acid.

17. The liposomal nanoparticles of claim 1, wherein the liposomal nanoparticles further comprise an imaging agent.

18. A method for administering a therapeutic, prophylactic, and/or diagnostic agent to a patient in need thereof, the method comprising administering an effective amount of the mucus-penetrating liposomal nanoparticles of claim 1.

19. The liposomal nanoparticles of claim 1, wherein the concentration of the stabilizer is between about 20 mole percent and about 40 mole percent of the total of the PEG-conjugated lipids, the lipids, and the stabilizer.

20. The liposomal nanoparticles of claim 1, wherein the concentration of the stabilizer is between about 30 mole percent and about 40 mole percent of the total of the PEG-conjugated lipids, the lipids, and the stabilizer.

* * * * *